United States Patent [19]

DeBernardis et al.

[11] Patent Number: 5,140,040
[45] Date of Patent: Aug. 18, 1992

[54] 1-AMINOMETHYL-1,2,3,4-TETRAHYDRONAPHTHALENES

[75] Inventors: John F. DeBernardis, Lindenhurst; Robert E. Zelle, Grayslake; Fatima Z. Basha, Lake Forest, all of Ill.

[73] Assignee: Abbott Laboratories, Abbott Park, Ill.

[21] Appl. No.: 788,008

[22] Filed: Nov. 5, 1991

Related U.S. Application Data

[60] Division of Ser. No. 470,210, Jan. 25, 1990, Pat. No. 5,109,015, which is a continuation-in-part of Ser. No. 555,501, Jan. 13, 1989, abandoned, which is a continuation-in-part of Ser. No. 144,364, Jan. 15, 1988, abandoned.

[51] Int. Cl.$^5$ .................. A61K 31/40; C07D 405/04; C07D 409/04; C07D 207/04
[52] U.S. Cl. .................................. 514/422; 548/517; 548/527; 548/577; 514/429
[58] Field of Search ............... 514/422, 429; 548/517, 548/527, 577

[56] References Cited

PUBLICATIONS

CA112:76644q Preparation of . . . antagonists. DeBernardis et al. p. 746, 1990.

Primary Examiner—Mary C. Lee
Assistant Examiner—Joseph K. McKane
Attorney, Agent, or Firm—Jerry F. Janssen

[57] ABSTRACT

The present invention includes compounds represented by the formula:

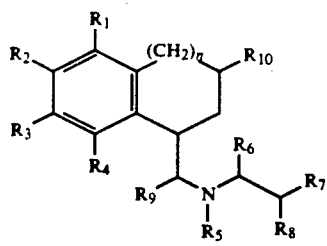

wherein n is 0 or 1; $R_1$, $R_2$, $R_3$, and $R_4$ are independently selected from hydrogen, hydroxyl, amino, alkylamino, alkylsulfonylamino, loweralkyl, loweralkoxy, halo, and thioalkoxy; $R_1$ and $R_2$ or $R_2$ and $R_3$ taken together can form a methylenedioxy or ethylenedioxy bridge; $R_{10}$ is independently selected from hydrogen, loweralkyl, phenyl, and substituted phenyl; $R_5$ is loweralkyl; $R_9$ is hydrogen or loweralkyl; $R_6$ and $R_8$ are hydrogen; and $R_7$ is

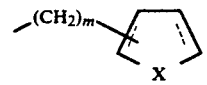

wherein m is 0, 1 or 2; X is $CH_2$, O, S or $N-CH_3$; or $R_7$ is

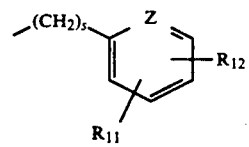

wherein s is 0, 1, or 2; Z is C or N; $R_{11}$ and $R_{12}$ are independently selected from hydrogen, halo, hydroxy, methoxy, thiomethoxy, amino and loweralkyl, or $R_{11}$ and $R_{12}$ taken together can form a methylenedioxy or ethylenedioxy bridge; or $R_7$ is

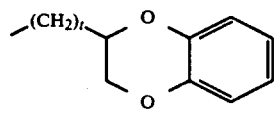

wherein t is 0 or 1; or $R_5$ and $R_9$ taken together form a pyrrolidine ring and $R_6$ and $R_8$ are hydrogen and $R_7$ is as described above; or $R_5$ and $R_9$ taken together form a pyrrolidine ring and then $R_6$ is hydrogen and $R_7$ and $R_8$ taken together may form a phenyl, substituted phenyl, thienyl or furyl ring; or $R_5$ and $R_8$ taken together form a pyrrolidine ring and then $R_9$ and $R_6$ are hydrogen and $R_7$ is phenyl, substituted phenyl, thienyl, or furyl; or $R_7$ and $R_9$ are hydrogen and $R_6$ is benzyl, substituted benzyl, thienylmethyl, or furylmethyl; or a pharmaceutically acceptable salt thereof.

5 Claims, No Drawings

1-AMINOMETHYL-1,2,3,4-TETRAHYDRONAPHTHALENES

This application is a divisional of copending application Ser. No. 470,210 filed Jan. 25, 1990 (now U.S. Pat. No. 5,109,015), which is a continuation in-part of application Ser. No. 555,501 filed Jan. 13, 1989, as PCT/US89/00140 (now abandoned) which, in turn, is a continuation of application Ser. No. 144,364, filed Jan. 15, 1988 (now abandoned).

TECHNICAL FIELD

This invention relates to alpha-2-adrenergic antagonists and biogenic amine uptake inhibitors which are useful in the treatment of depression, metabolic disorders (e.g. obesity or diabetes), glaucoma, migraine and hypertension.

BACKGROUND OF THE INVENTION

The adrenergic nervous system plays a major role in the innervation of heart, blood vessel and smooth muscle tissue. Compounds capable of interacting with receptor sites within the adrenergic nervous system can initiate a variety of physiological responses, including vasoconstriction, vasodilation, and increased or decreased heart rate (chronotropic), contractility (inotropic) and metabolic activity. In the past, various adrenergic compounds have been employed to affect these and other physiological responses. However, many adrenergic compounds do not possess significant selectivity to enable desirable interactions with adrenergic receptor sites. That is, these adrenergic compounds do not demonstrate a high degree of specificity for differing receptor types within the adrenergic nervous system in order to obtain a desired physiological response separate from other possible, and perhaps less desirable, responses of the system.

DeBernardis, et al., British Patent Application No. 2093837, published Sep. 8, 1982, discloses aminoalkyl mono- or disubstituted 1,2,3,4-tetrahydronaphthalenes with adrenergic and/or dopaminergic activity that are useful as antihypertensive agents. Related compounds are disclosed in the present invention, however the compounds of the present invention have unexpectedly high affinity for alpha-2-receptors. The compounds of the present invention are also biogenic amine uptake inhibitors. In addition, the compounds of the present invention are useful as antidepressants and antiglaucoma agents.

DISCLOSURE OF THE INVENTION

It has now been determined that a new class of compounds, as herein defined, demonstrate an ability to selectively inhibit (i.e., antagonize) alpha-2-adrenergic receptors which are mainly distributed on the membranes of central and peripheral adrenergic neurons and on the tissues innervated thereby.

In addition, the compounds of this invention inhibit the uptake of biogenic amines. As used herein, the term "biogenic amines" refers to one or more of the compounds selected from the group consisting of norepinephrine, serotonin, dopamine and the like.

Through inhibitory interaction with the alpha-adrenergic receptor in the peripheral nervous system, one can modulate the function of adrenergic neurons and hemodynamic equilibrium which is therapeutically useful in a multitude of cardiovascular indications such as hypertension, congestive heart failure, and a variety of vascular spastic conditions. Furthermore, the alpha-adrenergic antagonists and biogenic amine uptake inhibitors are useful in certain neurological and psychiatric disorders such as depression. In addition, the compounds of the present invention are useful for the treatment of glaucoma.

The present invention includes compounds represented by the formula:

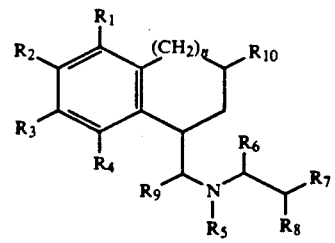

wherein n is 0 or 1;

$R_1$, $R_2$, $R_3$, and $R_4$ are independently selected from hydrogen, hydroxy, amino, alkylamino, alkylsulfonylamino, loweralkyl, loweralkoxy, halo, and thioalkoxy; or $R_1$ and $R_2$ or $R_2$ and $R_3$ taken together can form a methylenedioxy or ethylenedioxy bridge;

$R_5$ is loweralkyl;

$R_6$ and $R_8$ are hydrogen;

$R_7$ is

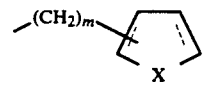

wherein m is 0, 1 or 2 and X is $CH_2$, O, S or N—$CH_3$;

or $R_7$ is

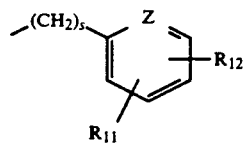

wherein s is 0, 1, or 2; Z is C or N; and $R_{11}$ and $R_{12}$ are independently selected from hydrogen, halo, hydroxy, methoxy, thiomethoxy, amino and loweralkyl, or $R_{11}$ and $R_{12}$ taken together can form a methylenedioxy or ethylenedioxy bridge;

or $R_7$ is

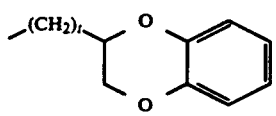

wherein t is 0 or 1;

$R_9$ is hydrogen or loweralkyl; and $R_{10}$ is hydrogen, loweralkyl, phenyl, or substituted phenyl wherein the phenyl ring is substituted with methylenedioxy, ethylenedioxy or with one, two or three substituents independently selected from loweralkyl, halo, hydroxy, loweralkoxy, amino and thioalkoxy; or $R_5$ and $R_9$ taken together form a pyrrolidine ring and then $R_6$ and $R_8$ are hydrogen and $R_7$ is

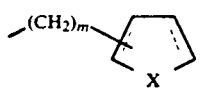

wherein
m is 0, 1 or 2 and X is $CH_2$, O, S or N—$CH_3$;
or $R_7$ is

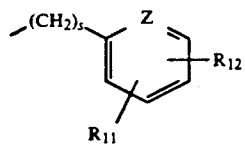

wherein
s is 0, 1, or 2; Z is C or N; and
$R_{11}$ and $R_{12}$ are independently selected from hydrogen, halo, hydroxy, methoxy, thiomethoxy, amino and loweralkyl, or $R_{11}$ and $R_{12}$ taken together can form a methylenedioxy or ethylenedioxy bridge;
or $R_7$ is

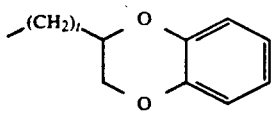

wherein
t is 0 or 1; or $R_5$ and $R_9$ taken together form a pyrrolidine ring and then $R_6$ is hydrogen and $R_7$ and $R_8$ taken together form a phenyl, thienyl, furyl or substituted phenyl wherein the phenyl ring is substituted with methylenedioxy, ethylenedioxy or with one, two or three substituents independently selected from loweralkyl, halo, hydroxy, loweralkoxy, amino and thioalkoxy; or $R_5$ and $R_8$ taken together form a pyrrolidine ring and then $R_9$ and $R_6$ are hydrogen and $R_7$ is phenyl, thienyl, furyl or substituted phenyl wherein the phenyl ring is substituted with methylenedioxy, ethylenedioxy or with one, two or three substituents independently selected from loweralkyl, halo, hydroxy, loweralkoxy, and thioalkoxy; or $R_7$ and $R_9$ are hydrogen and $R_6$ is benzyl, thienylmethyl, furylmethyl or substituted benzyl wherein the phenyl ring is substituted with methylenedioxy, ethylenedioxy or with one, two or three substituents independently selected from loweralkyl, halo, hydroxy, loweralkoxy, amino and thioalkoxy; or a pharmaceutically acceptable salt thereof.

It will be appreciated that the compounds of the present invention contain one or more asymmetric carbon atoms and it is to be understood that the invention includes the diastereomeric mixtures, the racemic mixtures, as well as the optically active compounds. As used herein, the designation "R*" or "S*" indicates the absolute configuration of the asymmetric center (i.e., the center is optically active), whereas the designation "R" or "S" indicates the relative configuration of the asymmetric center (i.e., the center is racemic).

As used in the structures shown above, the dashed lines mean that either a single or double bond may exist.

As used herein, the term "loweralkoxy" refers to alkoxy groups containing 1 or 2 carbon atoms.

As used herein, the term "thioalkoxy" refers to —SR″ wherein R″ is a loweralkyl residue.

As used herein, the term "loweralkyl" means straight or branched chain saturated hydrocarbon radicals having 1 to 3 carbon atoms, such as methyl, ethyl, n-propyl and iso propyl.

As used herein, the term "alkylamino" means —$NHR_{20}$ or —$NR_{20}R_{21}$ wherein $R_{20}$ and $R_{21}$ are independently selected from loweralkyl.

As used herein, the term "alkylsulfonylamino" means $R_{22}S(O)_2N(R_{23})$— wherein $R_{22}$ is loweralkyl and $R_{23}$ is hydrogen or loweralkyl.

As used herein, the term "substituted phenyl" means a phenyl ring with one, two or three substituents independently selected from loweralkyl, halo, hydroxy, loweralkoxy, amino, and thioalkoxy.

As used herein, the term "substituted benzyl" means a benzyl group wherein the pheny ring is substituted with one, two or three substituents independently selected from halo, loweralkoxy, thioalkoxy, loweralkyl, amino and hydroxy.

As used herein, the term "halo" or "halogen" means fluorine, iodine, bromine or chlorine.

The term "pharmaceutically acceptable salts" refers to the pharmaceutically acceptable, relatively nontoxic, inorganic or organic acid addition salts of the compounds of this invention. These salts can be prepared in situ during the final isolation and purification of the compounds, or by separately reacting the free base with a suitable organic or inorganic acid. Representative salts include the hydrochloride, hydrobromide, sulfate, phosphate, nitrate, bisulfate, acetate, oxalate, valerate, oleate, palmitrate, methanesulfonate, stearate, laurate, borate, benzoate, lactate, phosphate, tosylate, citrate, maleate, fumarate, succinate, tartrate, napsylate and the like. It will be apparent to those skilled in the art that, depending upon the number of available amino groups for salt formation, the salt of this invention can be per N-salts.

The compounds of the present invention can be prepared as illustrated in Schemes 1–4.

As seen in Scheme 1, starting with the appropriately substituted 1-tetralone, the dihydro-1-cyanonaphthylene derivative is obtained either with trimethylsilyl cyanide or diethylcyanophosphonate. Reduction to the corresponding aminomethyl tetralin is accomplished with Raney-Nickel to afford compound 1. If desired, the 1-carboxylic acid derivative is obtained after reduction with sodium borohydride, followed by hydrolysis, affording 2.

The amine 1 can be alkylated using the appropriate carboxylic acid or ester, activated ester or acid halide derivatives thereof, followed by reduction of the resulting amide bond. Acid halide derivatives include the acid chloride. Esters include the methyl and ethyl esters. Activated ester derivatives include activated esters commonly used by those skilled in the art for activating carboxylic acid groups for coupling with an amine to form an amide bond including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N hydroxybenzotriazole derived esters, 4-nitrophenol derived esters, 2,4,5-trichlorophenol derived esters and the like. In particular, as seen in Scheme 2, compound 1 can be N alkylated with ethyl formate, followed by diborane reduction of the amide, to give 3 or N-alkylated to the mono ethyl derivative with acetic anhydride, followed by diborane reduction, affording 4.

These secondary amines afford the desired products 5 or 6 upon dicyclohexylcarbodiimide (DCC) promoted coupling with the appropriately substituted carboxylic acids, followed by reduction of the amide intermediates with lithium aluminium hydride. Alkylation to provide 5 or 6 can also be accomplished using carboxylic acid derivatives such as acid halides, esters or activated esters, as described above, followed by reduction of the resulting amide.

As seen in Scheme 3, compound 2, upon coupling with DCC and the desired pyrrolidine derivative, affords 7 which upon reduction with diborane affords the desired pyrrolidine product 9. Carboxylic acid derivatives such as those described above can also be used in this process.

Alternatively, the pyrrolidine product 12 may be prepared from 2 following formation of the acid chloride with oxalyl chloride and subsequent formation of the carboxamide 8. Treatment of 8 with 2,2,5,5-tetramethyl-1-aza-2,5-disilacyclo pentane 1-propyl magnesium bromide affords 10 upon reduction with sodium borohydride. N-alkylation of the pyrrolidine is accomplished with DCC coupling with a carboxylic acid derivative and diborane reduction to give 12. Carboxylic acid derivatives such as those described above can also be used in this process.

Compound 8, upon reaction with the desired Grignard reagent and then an appropriately substituted amine in the presence of sodium cyanoborohydride, affords 11. DCC coupling of 11 and the desired carboxylic, acid followed by reduction with either diborane or lithium aluminum hydride, gives the product 13. Carboxylic acid derivatives such as those described above can also be used in this process.

As seen in Scheme 4, the desired 3-substituted 1-tetralones can be synthesized from the appropriate 1,3-dithiane derivative, which is formed from the corresponding substituted benzaldehyde. Addition of the dithiane anion to various cinnamates or acrylates provides the homologated ester. Raney nickel reduction and basic hydrolysis, followed by acidic cyclization, affords the desired 3-substituted 1-tetralones, which can be carried on as outlined in schemes 1-3.

Scheme 1

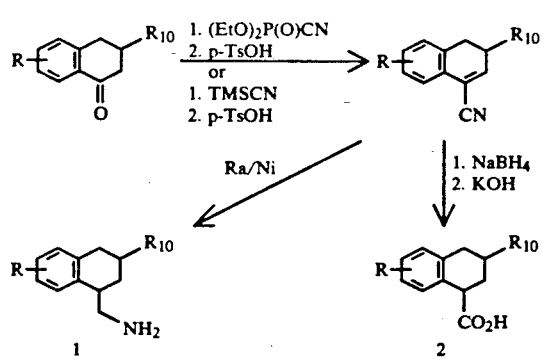

Scheme 2

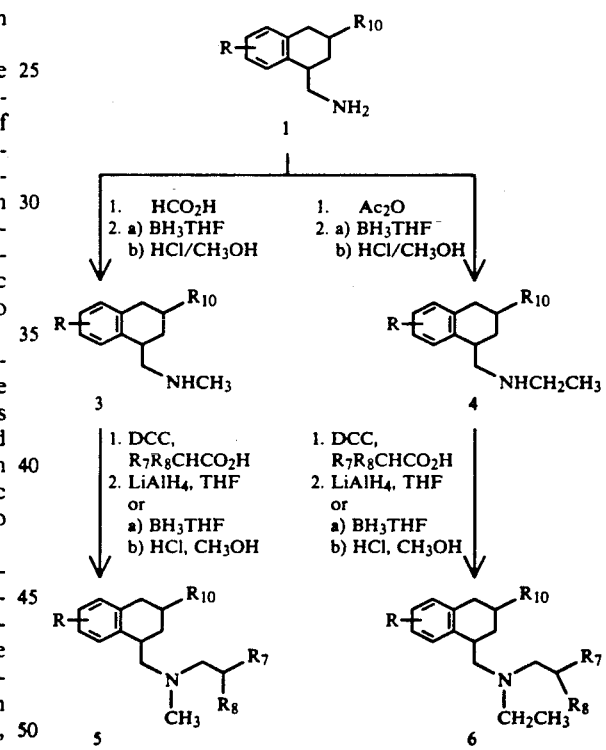

Scheme 3

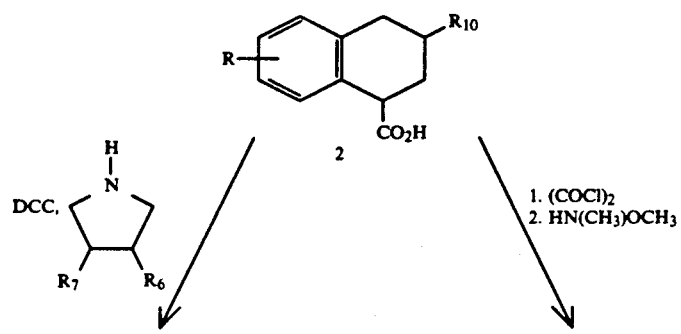

-continued
Scheme 3
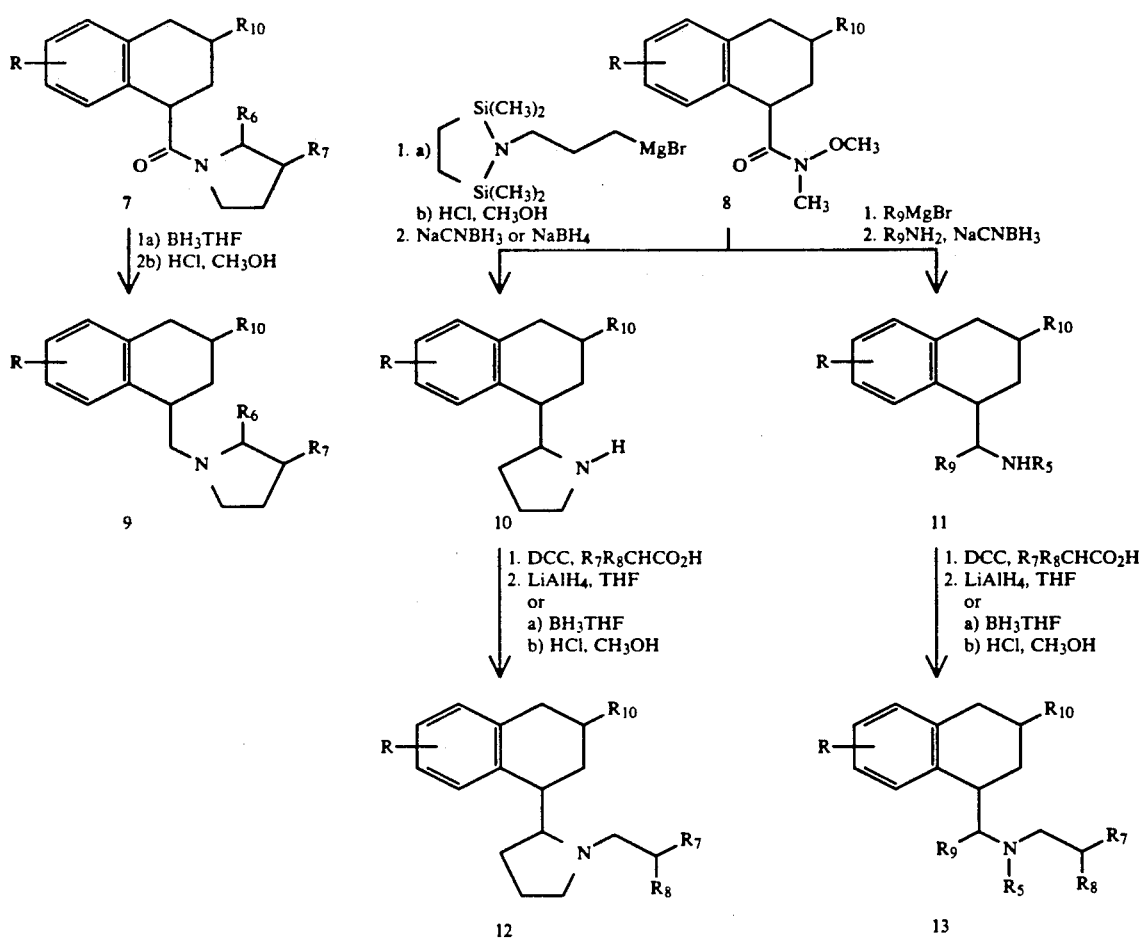
Scheme 4
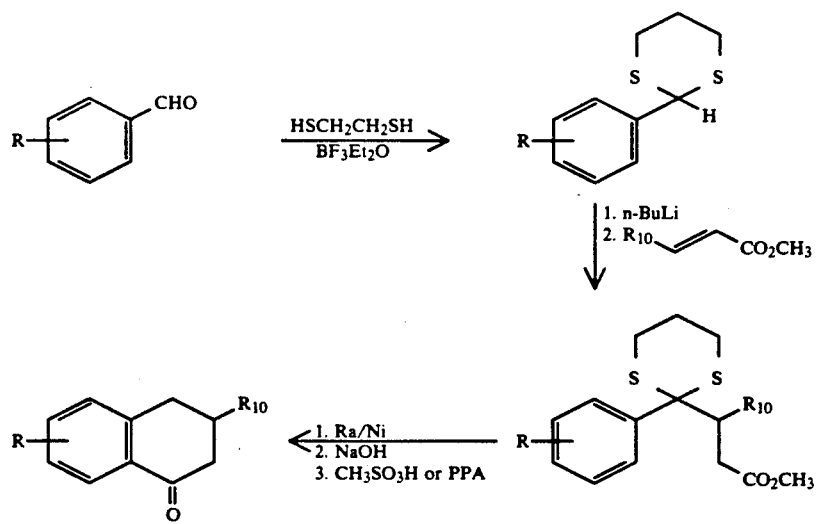
The foregoing may be better understood in connection with the following examples:

1-Cyano6-methoxy-3,4-dihydronaphthalene

To a refluxing benzene solution (60 ml) of 6-methoxy-1-tetralone was added trimethylsilyl cyanide (TMSCN) (67.5 g) and a trace of $AlCl_3$ or $ZnI_2$. Refluxing was continued for 1 hr., then the solvent removed under vacuum. Isopropyl alcohol saturated with HCl(g) was added and the solution refluxed for 1 hr. Precipitation began to occur and the reaction was cooled, then evaporated to dryness. Water was added, followed by an ethyl acetate (EtOAc) extraction. The organic layer was washed in sequence with 1 N NaOH, 1N HCl, and brine, separated, dried ($MgSO_4$), filtered and evaporated. The dark oil was chromatographed on silica gel and eluted with $CH_2Cl_2$, affording 98.5 g, 94% yield of product.

EXAMPLE 2

6-Methoxy-1-aminomethyl tetralin hydrochloride

The product (93 g) from Example 1 was hydrogenated at room temperature with RaNi (184 g) at 3 atm pressure in the presence of MeOH (900 ml) and $NH_3$ (100 ml). The solvent was evaporated, $H_2O$ and KOH added, followed by extraction with ethyl acetate. The organic layer was washed with brine, separated, dried ($MgSO_4$), filtered then isopropanol/HCl added. The desired product precipitated, was filtered and dried (87.7 g).

EXAMPLE 3

1-((N-Methylamino)methyl)-6-methoxytetralin hydrochloride

The product from Example 2 was converted to the free base (15 g) then dissolved in toluene (40 ml). Ethyl formate (70 ml) was added and the reaction refluxed for 2 hr. The solvent was evaporated giving an oil. This was dissolved in dry tetrahydrofuran (THF) (100 ml) and added dropwise to lithium aluminum hydride (3.23 g) in THF, with cooling. Upon complete addition, the reaction was refluxed for 2½ hr. then stirred an additional 24 hr at room temperature, followed by an additional 3 hrs refluxing. The mixture was cooled in an ice bath, then quenched with $H_2O$ (3.3 ml), 15% aq. KOH (3.3 ml) and $H_2O$ (9.9 ml) added dropwise. After stirring for 1 hr at room temperature, the reaction was filtered, and evaporated to dryness. The residue was converted to the HCl salt with ethereal/HCl giving 12.9 g desired product.

EXAMPLE 4

N-(6-Methoxy-1,2,3,4-tetrahydro-1-naphthyl)methyl-N-methyl 2-thienylacetamide

The product from Example 3 was converted to the free base (6 g) and dissolved in dry tetrahydrofuran (THF) (125 ml). Then 2-thiopheneacetic acid (3.62 g) and 1-hydroxybenzotriazole (5.1 g) was added followed by the dropwise addition of N,N'-dicyclohexylcarbodiimide (DCC) 6.7 g in dry THF (50 ml). The reaction was stirred at room temperature overnight, then filtered and evaporated to dryness. The oil was dissolved in EtOAc and upon standing precipitation occurred. This was filtered, and the filtrate washed with 1 N NaOH, then 1 N HCl and brine. The organic phase was dried ($MgSO_4$), filtered and concentrated to afford the product, 7.4 g, 91% yield.

EXAMPLE 5

1-((N-Methylamino)methyl-N-(2-(2-thienyl)ethyl))-6-methoxy tetralin methanesulfonate The product from Example 4 (7.2 g) was dissolved in dry THF (50 ml) then a 1 M solution of $BH_3$ in THF (65 ml) was added dropwise. The reaction was refluxed for 3 hrs., cooled, treated with 6N HCl (50 ml) added dropwise, and upon complete addition, refluxed for 2 hrs. The reaction was then allowed to stand overnight during which time a solid precipitated. This solid was filtered and dried giving 7.24 g of the hydrochloride salt, m.p. 211°–213° C. Anal.calcd. for $C_{19}H_{26}ClNOS$: C, 64.83; H, 7.46; N, 3.98. Found: C, 64.59; H, 7.40; N, 3.74.

The hydrochloride was converted to the free base and dissolved in EtOAc (50 ml), then methanesulfonic acid (1.1 ml) in EtOAc added. A solid separated, which was filtered giving the product, m.p. 129°–30° C. Anal.-calcd. for $C_{20}H_{29}NO_4S_2$: C, 58.35; H, 7.12; N, 3.40. Found: C, 58.23; H, 7.01; N, 3.36.

EXAMPLE 6

Using the product from Example 3 and utilizing the procedures described in Examples 4 and 5 substituting for the 2-thiopheneacetic acid the desired readily available carboxylic acid the following compounds were prepared:

6a) 1-((N-methylamino)methyl N-(2-(p-fluorophenyl)ethyl))-6-methoxy tetralin hydrochloride; m.p. 202°–4° C.

Anal. calcd. for $C_{21}H_{27}ClFNO$: C, 69.30; H, 7.49; N, 3.85. Found: C, 69.07; H, 7.43; N, 3.94.

b) 1-((N-methylamino)methyl-N-(2-(m-fluorophenyl)ethyl))-6-methoxy tetralin hydrochloride; m.p. 203°–5° C.

Anal. calcd. for $C_{21}H_{27}ClFNO$: C, 69.30; H, 7.49; N, 3.85. Found: C, 69.32; H, 7.59; N, 3.60.

c) 1-((N-methylamino)methyl-N-(2-phenylethyl))-6-methoxy tetralin hydrochloride; m.p. 206°–8° C.

Anal. calcd. for : $C_{21}H_{28}ClNO$: C, 72.90; H, 8.17; N, 4.05. Found: C, 72.70; H, 8.01; N, 3.81.

d) 1-((N-methylamino)methyl N-(2-(3-thienyl)ethyl))-6-methoxy tetralin hydrochloride; m.p. 215°–16° C.

Anal. calcd. for $C_{19}H_{26}ClNOS$: C, 64.83; H, 7.46; N, 3.98. Found: C, 64.88; H, 7.62; N, 3.99.

e) 1-((N-methylamino)methyl N-(4-(2-thienyl)butyl))6-methoxy tetralin hydrochloride; m.p. 172°–5° C.

Anal. calcd. for $C_{21}H_{30}ClNOS$: C, 66.38; H, 7.96; N, 3.69. Found: C, 66.22; H, 7.80; N, 3.24.

f) 1-((N- methylamino)methyl N-(2-(cyclopentyl)ethyl)) 6-methoxy tetralin hydrochloride; m.p. 189°–90° C.

Anal. calcd. for $C_{20}H_{32}ClNO$: C, 71.09; H, 9.54; N, 4.14. Found: C, 70.61; H, 9.64; N, 3.97.

g) 1-((N methylamino)methyl-N (2-(o-iodophenyl)ethyl)) 6-methoxy tetralin hydrochloride; m.p. 140°–41° C.

Anal. calcd. for $C_{21}H_{27}ClINO \cdot \frac{1}{2}H_2O$:C, 52.46; H, 5.87; N, 2.91. Found: C, 52.34; H, 5.75; .N, 2.97.

h) 1-((N-methylamino)methyl-N-(2-(2-tetrahydrothienyl) ethyl))-6-methoxy tetralin hydrochloride; m.p. 163°–64° C.

Anal. calcd. for $C_{19}H_{30}ClNSO$: C, 64.11; H, 8.49; N, 3.93. Found: C, 63.52; H, 8.54; N, 3.83.

i) 1-((N-methylamino)methyl N-(3-(2-thienyl)propyl)) 6-methoxy tetralin hydrochloride; m.p. 169°–70° C.

Anal calcd. for $C_{20}H_{28}ClNOS$: C, 65.64; H, 7.71; N, 3.83. Found: C, 65.51; H, 7.42; N, 3.78.

j) 1-((N-methylamino)methyl N-(3-phenylpropyl))-6-methoxy tetralin hydrochloride; m.p. 169°-70° C.

Anal calcd. for $C_{22}H_{30}ClNO$: C, 73.41; H, 8.40; N, 3.89. Found: C, 73.32; H, 8.57; N, 3.64.

k) 1-((N methylamino)methyl-N-(2-(m-methoxyphenyl)ethyl))-6-methoxy tetralin hydrochloride, M+291.

l) 1-((N-methylamino)methyl N-(2-(m-pyridyl)ethyl))6-methoxy tetralin dihydrochlorhde; m.p. 188°-89° C.

EXAMPLE 7

1-((N-Methylamino)methyl-N(2-(2-thienyl)ethyl))-6-hydroxy tetralin hydrochloride The product from Example 4 (2.35 g of the HCl salt) was added to $CH_2Cl_2$ (150 ml) and stirred at −78° C. while $BBr_3$ (2.2 ml) was added dropwise. Upon complete addition the reaction was allowed to warm to room temperature and stirred for 1 hr. After this period, the reaction was cooled to −78° C. and quenched by the careful addition of MeOH. The reaction was evaporated to dryness then dissolved in $MeOH/CH_2Cl_2$ and brought to pH7 with $NH_4OH$. The residue was chromatographed on silica gel and eluted with $CH_2Cl_2$ with increasing amounts of MeOH to a final concentration of 20% $MeOH/80\%$ $CH_2Cl_2$. The product was evaporated to dryness, dissolved in $Et_2O$, then ethereal HCl added. Upon evaporation a white solid was obtained which was crystallized from EtOAC-95%EtOH $Et_2O$ mixture affording the desired product. Anal. calcd. for $C_{18}H_{24}ClNOS$: C, 63.97; H, 7.17; N, 4.15. Found: C, 63.57; H, 7.22; N, 3.98.

EXAMPLE 8

1-((N-Methylamino)methyl-N-(2-(3-thienyl)ethyl))-6-hydroxy tetralin hydrochloride Using the compound from Example 6d with the procedure of Example 7 the desired compound was obtained m.p. 114°-16° C. Anal. calcd. for $C_{18}H_{24}ClNOS$: C, 63.97; H, 7.17; N, 4.15. Found: C, 63.57; H, 7.22; N, 3.98.

EXAMPLE 9

1-((N-Methylamino)methyl-N-(2-(p-fluorophenyl)ethyl))-6-hydroxy tetralin hydrobromide The product from Example 6a (1.6 g) was added to $CH_2Cl_2$ (30 ml) then cooled to −78° C. $BBr_3$ (1.5 ml) in 5 ml $CH_2Cl_2$ was added dropwise, and the reaction was stirred 3 hrs. At the end of this period, MeOH (10 ml) was carefully added and the solution was evaporated to dryness affording a brownish residue. This residue was dissolved in $CH_3CN$ and allowed to stand at room temperature overnight. A solid precipitated and was filtered then recrystallized from $CH_3CN$ affording the desired product, m.p. 129°-31° C. Anal. calcd. for $C_{20}H_{25}BrFNO$: C, 60.91; H, 6.40; N, 3.55. Found: C, 60.76; H, 6.42; N, 3.51.

EXAMPLE 10

1-((N-Methylamino)methyl-N-(2-(m-fluorophenyl)ethyl))6-hydroxy tetralin hydrochloride The product from Example 6b (.75 g) was O-demethylated with $BBr_3$ (0.7 ml) using the procedure of Example 9. However, after quenching the reaction with MeOH the solution was evaporated to dryness then methanolic HCl (20 ml) was added. This was heated on a steam bath until the volume was reduced to ca. 2-3 ml. The white solid was triturated with ethylacetate, filtered and dried giving the product, m.p. 154°-55° C. Anal. calcd. for $C_{20}H_{25}ClFNO$: C, 68.65; H, 7.22; N, 4.00. Found: C, 68.32; H, 7.22; N, 3.70.

EXAMPLE 11

1-((N-Methylamino)methyl-N-(2-phenylethyl))-6-hydroxy tetralin hydrobromide

Using the product from Example 6c with the procedure of Example 9 afforded the product, m.p. 156°-57° C. Anal. calcd. for $C_{20}H_{26}BrNO$: C, 63.82; H, 6.98; N, 3.72. Found:, C, 63.56; H, 6.84; N, 3.46.

EXAMPLE 12

1-((N-Methylamino)methyl-N-(2-(N-methyl2-pyrrolyl)-ethyl))-6-methoxy tetralin fumarate The desired compound (m.p. 145°-6° C.) was obtained using the procedures of Examples 1-5 but replacing 2-thiopheneacetic acid with N-methyl-2-pyrrolyl acetic acid and then preparing the fumarate salt in place of the HCl salt. Anal. calcd. for $C_{24}H_{32}N_2O_5$: C, 67.24; H, 7.53; N, 6.54. Found: C, 66.89; H, 7.54; N, 6.26.

EXAMPLE 13

5-Methoxy-3,4-dihydronaphthalene-1-carbonitrile

5-Methoxy-1-tetralone (8.80 g) was dissolved in 50 ml of anhydrous THF and cooled to 5° C. under $N_2$ atmosphere. LiCN (0.50 g.) was added to the stirred solution, followed by dropwise addition of diethyl cyanophosphonate (9.1 ml) over 10 min. After 45 min at 5° C., the reaction was poured into 200 ml $H_2O$ and extracted with EtOAc (3×100 ml). The combined organic extracts were washed with water (3×150 ml), saturated NaCl (150 ml), dried ($MgSO_4$), and evaporated under reduced pressure. The resulting colorless oil was dissolved in benzene (100 ml) and p-toluenesulfonic acid (0.50 g) was added. The reaction was stirred at reflux for 2 hr, cooled to room temperature, and poured into 5% $NaHCO_3$ solution (150 ml). The reaction was extracted with $Et_2O$ (2×100 ml) and the combined organic extracts were washed with saturated NaCl solution (150 ml), dried ($MgSO_4$), and evaporated under reduced pressure to yield 9.55 g of a white solid. The product was recrystallized from MeOH to yield 7.81 g of the product as white needles.

EXAMPLE 14

5-Methoxy-1-aminomethyl-tetralin hydrochloride

The product from Example 13 was hydrogenated using the procedure of Example 2 to give the desired product. Anal. calcd. for $C_{12}H_{18}ClNO$: C, 63.30; H, 7.91; N, 6.15. Found: C, 63.13; H, 8.15; N, 6.09.

EXAMPLE 15

1-((N-Ethylamino)methyl)-5-methoxy tetralin hydrochloride

The product from Example 14 was treated with KOH to give the free base, then reacted with acetic anhydride affording the amide. Anal. calcd. for $C_{14}H_{19}NO_2$: C, 72.07; H, 8.21; N, 6.00. Found: C, 72.03; H, 8.25; N, 6.01. This amide was reduced using the procedure of Example 5 to give the desired compound. Anal. calcd. for $C_{14}H_{22}ClNO$: C, 65.74; H, 8.67; N, 5.48. Found: C, 65.71; H, 8.61; N, 5.47.

EXAMPLE 16

1-((N-Formylamino)methyl)5-methoxytetralin

The product from Example 14 was converted to its free base (3.4 g) and dissolved into toluene (30 ml). Ethyl formate (5 ml) was added and the reaction stirred at reflux for 5 hr. The solvent was removed to afford a solid. Recrystallization from $Et_2O/CH_2Cl_2$ afforded 3.07 g of desired product. Anal. calcd. for $C_{13}H_{17}NO_2$; C, 71 21; H, 7.81; N, 6.39. Found: C, 71.26; H, 7.82; N, 6.41.

EXAMPLE 17

1-((N-Methylamino)methyl)5-methoxytetralin hydrochloride

The product from Example 16 (3.8 g) in dry THF (80 ml) was treated with 1 M solution of $BH_3$ in THF (38 ml). After the addition was complete, the reaction was heated at reflux for 1 hr, followed by cooling. The reaction was treated with saturated methanolic HCL (30 ml), heated at reflux for 1 hr and concentrated to afford a solid. Crystallization from $Et_2O/ CH_3OH$ afforded 4.1 g of desired product. Anal. calcd. for $C_{13}H_{20}ClNO$: C, 64.59; H, 8.34; N, 5.79. Found: C, 64.68; H, 8.49; N, 5.78.

EXAMPLE 18

N-(5-Methoxy-1.2,3,4-tetrahydro-1-naphthyl)methyl-N-methyl-2-thienylacetamide

The product from Example 17 (1.04 g), 1-hydroxybenzotriazole hydrate (1.51 g) and 2-thiopheneacetic acid (720 mg) in dry THF (30 ml) at 0° C. was treated with dicyclohexylcarbodiimide (1.16 g). The reaction was warmed to room temperature and stirred for 18 hr. The mixture was filtered and concentrated. The residue was dissolved into EtOAc (60 ml) washed with 5% aq. HCl (15 ml), water (15 ml), 10% aq. KOH (15 ml), dried ($MgSO_4$) filtered and concentrated. Chromatography on $SiO_2$ afforded 1.58 g of product as a viscous oil.

EXAMPLE 19

1-((N-Methylamino)methyl-N-(2-(2-thienyl)ethyl))-5-methoxy tetralin methanesulfonate The product from Example 18 (1.58 g) in dry THF (10 ml) was slowly added to a suspension of lithium aluminum hydride (366 mg) in dry THF (30 ml) and the resulting mixture heated at reflux for 1 hr. The reaction was cooled and treated with water (370uL), 15% aq. KOH (370 uL) and water (1.1 mL). After 30 min, the mixture was filtered and the filtrate concentrated. Chromatography on $SiO_2$ afforded 1.02 g of product as a viscous oil. The oil was dissolved into EtOAc(30 ml) and treated with a solution of methanesulfonic acid (300 uL) in i-PrOH(700 uL). Crystallization occurred upon standing to afford 1.17 g of desired product, m.p. 178°-79° C. Anal. calcd. for $C_{20}H_{29}NO_4S_2$: C, 58.37; H, 7.10; N, 3.40. Found: C, 58.10; H, 7.16; N, 3.39.

EXAMPLE 20

Using the product from Example 17 and utilizing procedures described in Examples 18 and 19 substituting for the 2-thiopheneacetic acid the desired readily available carboxylic acid the following compounds were prepared:

20 a) 1-((N-methylamino)methyl-N-2-(2-furyl)ethyl))-5-methoxytetralin methanesulfonate, m.p. 154°-55° C.
Anal. calcd. for $C_{20}H_{29}NO_5S$: C, 60.74; H, 7.39; N, 3.54. Found: C, 60.36; H, 7.45; H, 3.52.

b) 1-((N-methylamino)methyl-N-(2-(p-fluorophenyl)ethyl))-5-methoxytetralin methanesulfonate c) 1-((N-methylamino)methyl-N-(2-(m-fluorophenyl)ethyl))-5-methoxytetralin methanesulfonate, m.p. 180°-181° C. Anal. calcd. for $C_{22}H_{30}FNO_4S$: C, 62.39; H, 7.14; N, 3.31. Found: C, 62.36; H, 7.08; N, 3.31.

EXAMPLE 21

1-((N-Methylamino)methyl-N-(2-(2-furyl)ethyl))-6-methoxy tetralin hydrochloride

Reacting the product from Example 3 with 2-furylacetic acid using the procedures of example 18 gave the desired amide. The amide was reduced using the procedure of example 19 except the hydrochloride salt was prepared with ethereal HCl in place of methanesulfonic acid, affording the compound, m.p. 203°-5° C. Anal. calcd. for $C_{19}H_{26}ClNO_2$ C, 67.94; H, 7.80; N, 4.17. Found: C, 67.93; H, 7.90; N, 4.07.

EXAMPLE 22

1-((N-Methylamino)methyl-N-(2-(2-thienyl)ethyl)) tetralin hydrochloride

The desired compound was prepared (m.p. 222°-23° C.) using the procedures described in Examples 1–5 but replacing 6-methoxy-1-tetralone with 1-tetralone. Anal. calcd. for $C_{18}H_{24}ClNS$: C, 67.16; H, 7.51; N, 4.35. Found: C, 66.76; H, 7.82; N, 4.34.

EXAMPLE 23

1-((N-Methylamino)methyl-N-(2-(2-thienyl)ethyl))-5,6-methylenedioxy tetralin hydrochloride The desired compound was prepared (m.p. 248°-49° C.) using the procedures described in Examples 1–5 but replacing 6-methoxy-1-tetralone with 5,6-methylenedioxy-1-tetralone. Anal. calcd. for $C_{19}H_{24}ClNO_2S$ C, 62.38; H, 6.57; N, 3.83. Found: C, 62.06; H, 6.57; N, 3.56.

EXAMPLE 24

1-((N-Methylamino)methyl-N-(2-(m-methoxyphenyl)ethyl))-5,6-dimethoxy tetralin hydrochloride The product was obtained (m.p. 160°-61° C.) using the procedures described in Examples 1–5 but replacing 6-methoxy1-tetralone with 5,6-dimethoxy-1-tetralone, and using 3-methoxyphenylacetic acid, in place of 2-thiopheneacetic acid. Anal. calcd. for $C_{23}H_{32}ClNO_3$: C, 68.05; H, 7.95; N, 3.45. Found: C, 68.07; H, 7.99; N, 3.24.

EXAMPLE 25

1-((N-Methylamino)methyl-N-(2-(2-thienyl)ethyl))-6,7-dimethoxy tetralin hydrochloride The product was obtained (m.p. 149°-50° C.) using the procedures described in Examples 1–5 but replacing 6-methoxy1-tetralone with 6,7-dimethoxy-1-tetralone. Anal. calcd. for $C_{20}H_{28}ClNO_2S$: C, 62.89; H, 7.39; N, 3.67. Found: C, 62.87; H, 7.23; N, 3.54.

EXAMPLE 26

1-((N-Methylamino)methyl-N-(2-(2-thienyl)ethyl))-6,8-dimethoxy tetralin hydrochloride The product was obtained (m.p. 210°-12° C.) using the procedures described in Examples 1–5 but replacing 6-methoxy-1-tetralone with 6,8-dimethoxy1-tetralone.

Anal. calcd. for $C_{20}H_{28}ClNO_2S$ C, 62.89; H, 7.39; N, 3.67. Found: C, 62.55; H, 7.50; N, 3.51.

EXAMPLE 27

1-((N-Methylamino)methyl-N-(2-(2-thienyl)ethyl))-7-methoxy tetralin hydrochloride The product was obtained (m.p. 180°14 1° C.) using the procedures described in Examples 1-5 but replacing 6-methoxy-1-tetralone with 7-methoxy-1-tetralone. Anal. calcd. for $C_{19}H_{26}ClNOS$ C, 64.84; H, 7.45; N, 3.98. Found: C, 64.74; H, 7.28; N, 3.88.

EXAMPLE 28

1-((N-Methylamino)methyl-N-(2-phenylethyl))-7-methoxy tetralin hydrochloride

The product was prepared (m.p. 178°-79° C.) using the procedures described in Examples 1-5 but replacing 6-methoxy-1-tetralone with 7-methoxy-1-tetralone, and using phenylacetic acid, in place of 2-thiopheneacetic acid. Anal. calcd. for $C_{21}H_{28}ClNO$; C, 72.92; H, 8.16; N, 4.05. Found: C, 72.27; H, 8.09; N, 3.87.

EXAMPLE 29

5,6-Ethylenedioxy-1-tetralone 5,6-Dihydroxy-1-tetralone (6 g) was heated at 125° C. with 1,2-dichloroethane (7 ml) and $K_2CO_3$ (14 g) in DMSO (70 ml) under $N_2$ for 45 min. The reaction was quenched with ice water then extracted with $Et_2O$. The aqueous layer was removed, then EtOAc added to the remaining organics. This solution was dried ($MgSO_4$), filtered and evaporated to give the desired product.

EXAMPLE 30

1-((N-Methylamino)methyl-N-(2-(2-thienyl)ethyl))-5,6-ethylenedioxy tetralin hydrochloride The product was prepared (m.p. 205°-6° C.) using the procedures described in Examples 1-5 but replacing 6-methoxy-1-tetralone with the product from Example 29. Anal. calcd. for $C_{20}H_{25}ClNO_2S$: C, 63.39; H, 6.65; N, 3.70. Found: C, 62.96; H, 6.99; N, 3.66.

EXAMPLE 31

6-Thiomehtyl-1-tetralone

6-Hydroxy-1-tetralone (16.2 g) prepared from 6-methoxy-1-tetralone and $AlCl_3$, was dissolved in dry dimethylformamide (DMF)(50 ml) and added dropwise to a suspension of 4 g NaH (60% in mineral oil) and dry DMF (200 ml) over 30 min. Then, dimethylthiocarbamyl chloride (14.8 g) was added and the reaction heated at 85° C. for 4 hrs. The reaction was poured onto ice and extracted with $CH_2Cl_2$ (150 ml). The $CH_2Cl_2$ layer was washed with 10% aq. NaOH, then saturated NaCl solution. The organic layer was separated, dried $Na_2SO_4$), filtered and evaporated giving a tan solid (18.1 g). This was added to mineral oil (100 ml) and heated at 270° C. for 2 hrs, then cooled. Cyclohexane (500 ml) was added and a solid separated (14.3 g). This product was added to NaOH (10 g) and MeOH (150 ml) and refluxed 2 hrs. The reaction was cooled, then methyliodide (9.94 g) was added followed by refluxing for 2 hrs. The solvents were removed affording the desired product (11 g), $M+192$.

EXAMPLE 32

1-((N-Methylamino)methyl-N-(2-(2-thienyl)ethyl))-6-thiomethyl tetralin hydrochloride The product was prepared (m.p. 206°-7° C.) using the procedures described in Examples 1-5 but replacing 6-methoxy-1-tetralone with the product of Example 31. Anal. calcd. for $C_{19}H_{25}ClNS_2 \cdot \frac{1}{4} H_2O$: C, 60.69; H, 6.97; N, 3.73. Found: C, 60.76; H, 7.12; N, 3.64.

EXAMPLE 33

1-((N-Methylamino)methyl-N-(2-(m-fluorophenyl)ethyl))-5,6-dimethoxy-8-methyl tetralin hydrochloride The product was obtained (m.p. 184°-86° C.) using the procedures described in Examples 1-5 but replacing 6-methoxy-1-tetralone with 5,6-dimethoxy-8-methyl-1-tetralone and using 3-fluorophenylacetic acid, in place of 2-thiopheneacetic acid. Anal. calcd. for $C_{23}H_{31}ClFNO_2$: C, 67.72; H, 7.66; N, 3.43. Found: C, 67.31; H, 7.88; N, 3.37.

EXAMPLE 34

1-(N-Methylamino)methyl-N-(2-(m-fluorophenyl)ethyl))-5,6-dihydroxy-8-methyl tetralin hydrobromide Using the product of Example 33 and the producer of Example 9 the desired compound was obtained m.p. (129°-30° C.). Anal. calcd. for $C_{21}H_{27}BrFNO_2 \cdot \frac{1}{2} H_2O$: C, 8.20; H, 6.40; N, 3.23. Found C, 58.45; H, 6.33; N, 3.02.

EXAMPLE 35

1-(N-Methylamino)methyl-N-(2-(2-thienyl)ethyl))-5,6-dimethoxy-8-methyl tetralin hydrochloride The product was obtained (M+359) using the procedures described in Examples 1-5 but replacing 6-methoxy-1-tetralone with 5,6-dimethoxy-8-methyl-1-tetralone.

EXAMPLE 36

1-(N-Methylamino)methyl-N-(2-(2-thienyl)ethyl))-5-methoxy-8-methyl tetralin hydrochloride The product was obtained (m.p. 205°-7° C.) using the procedures described in Examples 1-5 but replacing 6-methoxy-1-tetralone with 5-methoxy-8-methyl-1-tetralone. Anal. calcd. for $C_{20}H_{28}ClNOS$: C, 65.64; H, 7 71; N, 3.83. Found: C, 65.36; H, 7.90; N, 3.77.

EXAMPLE 37

1-((N-Methylamino)methyl-N-(2-(2-thienyl)ethyl))-5-methoxy indane hydrochloride

The product was obtained (m.p. 197°-99° C.) using the procedures described in Examples 1-5 but replacing 6-methoxy-1-tetralone with 5-methoxy-1-indanone. Anal. calcd. for $C_{18}H_{24}ClNSO$: C, 63.98; H, 7.16; H, 4.15. Found: C, 64.36; H, 7.19; N, 4.00.

EXAMPLE 38

6-Methoxy-7-methyl-1-tetralone

3-Methoxy-4-methylbenzoic acid (30 g) was reduced to the benzylic alcohol with BH3 in THF (181 ml of 1 M solution). Oxidation of this product (28.7 g) with pyridinium chlorochromate (71 g) gave the benzaldehyde derivative (21.3 g). Treatment of this aldehyde (19.6 g) with BrPh P(CH ) COOH (54.5 g) under Wittig conditions afforded 4-(3-methoxy-4-methylphenyl)-3- butene carboxylic acid (26.9 g). Catalytic reduction of this product followed by polyphosphoric acid (PPA) cyclization gave the desired tetralone.

EXAMPLE 39

1-((N-Methylamino)methyl-N-(2-(2-thienyl)ethyl))-6-methoxy-7-methyl tetralin hydrochloride The product was obtained (m.p. 173°-4° C.) using the procedures described in Examples 1-5 but replacing 6-methoxy-1-tetralone with the product of Example 38. Anal. calcd. for $C_{20}H_{28}NOS$: C, 65.64; H, 7.71; H, 3.83. Found: C, 65.47; H, 7.56; N, 3.66.

EXAMPLE 40

1-((N-Ethylamino)methyl)-6-methoxy tetralin hydrochloride

Using the product of Example 2 and the procedure of Example 15 afforded the desired compound.

EXAMPLE 41

1-((N-Ethylamino)methyl-N-(2-(2-thienyl)ethyl))-6-methoxy tetralin hydrochloride Using the product of Example 40 and the procedures of Examples 4 and 5 gave the desired compound m.p. 184°-85° C. Anal. calcd. for $C_{20}H_{28}ClNOS$: C, 65.64; H, 7.71; N, 3.83. Found: C, 65.48; H, 7.75; N, 3.79.

EXAMPLE 42

1-((N-Ethylamino)methyl-N-(2-(m-fluorophenyl)ethyl))-6-methoxy tetralin hydrochloride Using the product of Example 40 and the procedure of Examples 4 and 5 replacing 2thiopheneacetic acid with m-fluoroacetic acid gave the desired compound, m.p. 153°-54° C. Anal. calcd. for $C_{22}H_{29}ClFNO$: C, 70.37; H, 7.73; N, 3.71. Found: C, 70.37; H, 7.93; N, 3.70.

EXAMPLE 43

1-((N-Ethylamino)methyl-N-(2-(2-furyl)ethyl))-6-methoxy tetralin hydrochloride

Using the product of Example 40 and the procedure of Examples 18 and 19, replacing 2-thiopheneacetic acid with 2-furylacetic acid and replacing the methanesulfonic acid with ethereal HCl gave the compound, m.p. 176°-7° C. Anal. calcd. for $C_{20}H_{28}ClNO_2$: C, 68.65; H, 8.07; N, 4.00. Found: C, 68.58; H, 8.12; N, 4.00.

EXAMPLE 44

1-N-Ethylamino)methyl-N-(2-(3-thienyl)ethyl))-6-methoxy tetralin hydrochloride

Using the product of Example 40 and the procedure of Examples 4 and 5 replacing 2-thiopheneacetic acid with 3-thiopheneacetic acid gave the compound, m.p. 159°-60° C. Anal. calcd. for $C_{20}H_{28}ClNOS \cdot \frac{1}{4} H_2O$; C, 64.84; H, 7.75; N, 3.78. Found: C, 64.93; H, 7.63; N, 3.77.

EXAMPLE 45

1-((N-Methylamino)methyl-N-(2-(2-thienyl)ethyl))-6-methoxy indane hydrochloride

Using the procedures described in Examples 1-5 but replacing 6-methoxy-1-tetralone with 6-methoxy-1-indanone gave the product, m.p. 176°-7° C. calcd. for $C_{18}H_{24}ClNSO$: C, 63.98; H, 7.16; N, 4.15. Found: C, 63.73; H, 7.22; N, 4.13.

EXAMPLE 46

6-Chloro-3,4-dihydronaphthalene-1-carbonitrile

Using the procedure of Example 13 replacing 5-methoxy-1-tetralone with 6-chloro-1-tetralone afforded the desired product.

EXAMPLE 47

6-Chloro1-aminomethyl tetralin hydrochloride

The product from Example 46 was catalytically reduced with $Pt_2O$ at 4 atms. pressure in EtOH and HCl, the desired product.

EXAMPLE 48

1-((N-Methylamino)methyl)-6-chloro tetralin hydrochloride

Using the product of Example 47 and the procedure of Example 3 gave the desired compound.

EXAMPLE 49

1-((N-Methylamino)meth-N-(2-(2-thienyl)ethyl))-6-chloro tetralin hydrochloride

Using the product from Example 48 and the procedures of Examples 4 and 5 afforded the desired compound, m.p. 233°-34° C. Anal. calcd. for $C_{18}H_{23}Cl_2NS$: C, 60.67; H, 6.46; N, 3.93. Found: C, 60.61; H, 6.54; N, 3.90.

EXAMPLE 50

1-((N-Methylamino)methyl-N-(2-(2-thienyl)ethyl))-6-fluoro tetralin hydrochloride Using the procedures described in Example 13, then in Examples 46-48 replacing 6-chloro-1-tetralone with 6-fluoro-1-tetralone gave 1-(N-methylamino) methyl6-fluoro tetralin hydrochloride. Using this product and following the procedures of Examples 4 and 5 gave the desired compound, m.p. 225°-27° C. Anal. calcd. for $C_{18}H_{23}ClFNS$: C, 63.62; H, 6.77; N, 4.12. Found: C, 63.93; H, 7.05; N, 4.11.

EXAMPLE 51

5-Bromo-1-tetralone

To a benzene solution (60 ml) of 4-(o-bromophenyl) butyric acid (5 g) was added oxalyl chloride (3.6 ml) and the reaction refluxed for 1½ hrs. The solution was evaporated to dryness, the residue was dissolved in $CH_2Cl_2$ (50 ml) then cooled to 0° C., followed by the addition of $AlCl_3$ (3.1 g). The mixture was stirred at 0° C. warming to room temperature overnight. The reaction was poured onto ice, then extracted with $CH_2Cl_2$. The organic layer was separated, washed with 1 N NaOH, then brine, separated, dried ($MgSO_4$), filtered and evaporated affording the desired product (4.26 g).

EXAMPLE 52

5-Bromo-1,2,3,4-tetrahydronaphthalene-1-carbonitrile

Using the product from Example 51 (10 g) and the procedure of Example 1 gave 5-bromo-3,4 dihydronaphthalene-1-carbonitrile (8.5 g). This was reduced to the desired product with $NaBH_4$ (8.5 g) in ethanol (165 ml), under reflux conditions for 2 hrs.

EXAMPLE 53

5-Bromo-1-aminomethyl tetralin hydrochloride

The product from Example 52 (5 g) was reduced with diborane as in Example 5 and afforded the desired product after recrystallization from EtOH.

EXAMPLE 54

1-((N-Methylamino)methyl)-5-bromo tetralin hydrochloride

The product from Example 53 was reacted as in the procedure described in Example 3 and gave the desired compound, m.p. 224°–226° C. Anal. calcd. for $C_{12}H_{17}BrClN$: C, 49.59; H, 5.90; H, 4.82. Found: C, 49.73; H, 5.97; N, 4.81.

EXAMPLE 55

1-((N-Methylamino)methyl-N-(2-(2-furyl(ethyl))-5-bromo tetralin methanesulfonate Reacting the product of Example 54 with 2-furylacetic acid using the procedure of Example 4 gave the desired amide. This amide was reduced using the procedure of Example 19 giving the desired compound, m. p. 98°–99° C. Anal. calcd. for $C_{19}H_{26}BrNO_4S$: C, 51.35; H, 5.90; N, 3.15. Found: C, 51.75; H, 6.00; N, 3.14.

EXAMPLE 56

1-((N-Methylamino)methyl-N-(2-(2-furyl)ethyl))-6-bromo tetralin methanesulfonate Using the procedures described in examples 52–55 but replacing 5-bromo-1-tetralone with 6-bromo-1-tetralone afforded the desired compound, m.p. 95°–97° C. Anal. calcd. for $C_{19}H_{26}BrNO_4S$: C, 51.35; H, 5.90; N, 3.15. Found: C, 50.96; H, 5.93; N, 3.06.

EXAMPLE 57

1-((N-Propylamino)methyl)-6-methoxy tetralin hydrochloride

The product from Example 2 was reacted as in Example 15 but replacing acetic anhydride with propionic anhydride and gave the desired product.

EXAMPLE 58

1-((N propylamino)methyl)-N-(2-(2-thienyl)ethyl))-6-methoxy tetralin hydrochloride Using the product of Example 57 and the procedure of Examples 4 and 5 gave the compound (amorphous). Anal. calcd. for $C_{21}H_{30}ClNOS \cdot \frac{1}{4} H_2O$: C, 66.60; H, 8.00; N, 3.64. Found: C, 65.78; H, 7.78; N, 3.59.

EXAMPLE 59

1-((N-Methylamino)methyl)-N-(2-(2-thienyl)ethyl))-5-fluoro indane hydrochloride Using the procedures described in Example 13, and 46–48 but replacing the 6-methoxy-1-tetralone with 5-fluoro-1-indanone gave the product, m.p. 200°–2° C. Anal. calcd. for $C_{17}H_{21}ClFNS$: C, 62.66; H, 6.50; N, 4.30. Found: C, 62.37; H, 6.45; N, 3.98.

EXAMPLE 60

5-Hydroxy-6-iodo-1-indanone

5-Hydroxy-1-indanone (1.48 g), N-iodosuccinimide (2.25 g) and $CH_3CN$ (20 ml) were stirred at room temperature overnight. The solution was evaporated to dryness, slurried with EtOAc, then filtered. The filtrate was evaporated to dryness and the solid recrystallized from $CH_3CN$ affording the desired compound (0.92 g), m.p. 114°–15° C.

EXAMPLE 61

5-Methoxy-6-iodo-1-indanone

The product of Example 60 was added to methyl ethyl ketone (50 ml), $K_2CO_3$ (5 g) and methyl iodide (5 ml) then heated at reflux for 4½ hrs. The reaction was cooled, $H_2O$ added, followed by an EtOAc extraction. The organic layer was separated, washed with brine, dried ($Na_2SO_4$), filtered and evaporated. Trituration of the residue afforded the desired compound after filtration, m.p. 129°–30° C.

EXAMPLE 62

1-((N-Methylamino)methyl)-N-(2-(2-furyl)ethyl))-5-methoxy6-iodo indane methanesulfonate Using the product from Example 61 and the procedures described in Examples 13, 14 and 16–19 replacing 2-thiopheneacetic with 2-furylacetic acid afforded the desired product.

EXAMPLE 63

1-((N-Propylamino)methyl)-5,6-dimethoxy tetralin hydrochloride

Using the procedure of Example 57 but replacing 6-methoxy-1-tetralone with 5,6-dimethoxy-1-tetralone gave the desired product.

EXAMPLE 64

1-((N-Propylamino)methyl)-N-(2-(p-fluorophenyl)ethyl))-5,6-dihydroxy tetralin hydrobromide Using the product of Example 63 and the procedures described in Examples 4 and 5 replacing the 2-thiopheneacetic acid with 4-fluorophenylacetic acid gave 1-((N-propylamino)methyl)-N-(2-(p-fluorophenyl)ethyl))-5,6-dimethoxy tetralin hydrochloride. This product was reacted as described in Example 9 to give the desired product, m.p. 212°–14° C. Anal. calcd. for $C_{22}H_{29}BrFNO_2$: C, 60.27; H, 6.68; N, 3.20. Found: C, 60.26; H, 6.58; N., 3.19.

EXAMPLE 65

1-((N-Methylamino)methyl)-N-(2-(m-nitrophenyl)ethyl)) tetralin hydrochloride Using the procedures described in Examples 1–5 but replacing 6-methoxy-1-tetralone with 1-tetralone and replacing 2-thiopheneacetic acid with 3-nitrophenylacetic acid gave the desired compound.

EXAMPLE 66

1-((N-Methylamino)methyl)-N-(2-(m-aminophenyl)ethyl))-tetralin dihydrochloride The product from Example 65 (3 g) was catalytically reduced with 5% Pd/C at 3 atms. pressure in MeOH (95 ml) and $CHCl_3$ (5 ml) affording the desired amorphous dihydrochloride. Anal. calcd. for $C_{20}H_{27}Cl_2N \cdot \frac{1}{4} H_2O$: C, 63.81; H, 7.78; N, 7.44. Found: C, 63.35; H, 7.67; N, 7.38.

EXAMPLE 67

1 ((N-Methylamino)methyl-N-(2-(m aminophenyl)ethyl))-6-methoxy tetralin dihydrochloride Using the product of Example 3 and the procedures of Example 4, 5 and 66 the product was obtained, after recrystallization from EtOAc/EtOH. Anal calcd. for $C_{21}H_{30}Cl_2N_2O$. ½ $H_2O$: C, 62.05; H, 7.70; N, 6.89. Found: C, 62.15; H, 7.83; N, 6.51.

EXAMPLE 68

1-((N-Methylamino)methyl N-(2-(m-aminophenyl)ethyl))-6-hydroxy tetralin dihydrobromide The product from Example 67 (1.1 g) was reacted with $BBr_3$ (1.4 ml) as in the procedure of Example 9 and gave the desired product. Anal. calcd. for $C_{20}H_{28}Br_2N_2O$: C, 61.21; H, 7.46; N, 7.14. Found: C, 60.75; H, 7.45; N, 6.89.

EXAMPLE 69

1-((N-Methylamino)methyl-N-(2-(m-aminophenyl)ethyl))-6-ethoxy tetralin dihydrochloride Using the procedures described in Examples 1–5 but replacing 6-methoxy-1-tetralone with 6-ethoxy-1-tetralone and replacing 2-thiopheneacetic acid with 3-nitrophenylacetic acid gave the nitro derivative which was reduced as in Example 66. The product was obtained as an amorphous solid. Anal. calcd. for $C_{22}H_{32}Cl_2N_2O$.½ $H_2O$: C, 62.84; H, 7.93; N, 6.66. Found: C, 63.06; H, 7.82; N, 6.47.

EXAMPLE 70

1-((N-Methylamino)methyl-N-(2-(m-fluorophenyl)ethyl))-tetralin hydrochloride

Using the procedures described in Examples 1–5 but replacing 6-methoxy-1-tetralone with 1-tetralone and replacing 2-thiopheneacetic acid with m-fluorophenyl acetic acid gave the desired product, m.p. 198°–99° C. Anal. calcd. for $C_{20}H_{25}ClFN$: C, 71.94; H, 7.56; N, 4.20. Found: C, 72.33; H, 7.53; N, 3.86.

EXAMPLE 71

1-((N-Ethylamino)methyl-N-(2-(2-furyl)ethyl))-5-methoxy tetralin methanesulfonate Using the product (free base) of Example 15 and the procedures described in Examples 18 and 19 but replacing 2-thiopheneacetic acid with 2 furylacetic acid gave the desired compound.

EXAMPLE 72

1-((N-Ethylamino)methyl-N-(2-(m-fluorophenyl)ethyl))-5-methoxy tetralin hydrochloride Using the product (free base) of Example 15 and the procedures described in Examples 18 and 19 but replacing 2-thiopheneacetic acid with m-fluorophenyl acetic acid gave the desired compound, m.p. 177°–78° C. Anal. calcd. for $C_{22}H_{29}ClFNO$: C, 69.72; H, 7.73; N, 3.71. Found: C, 69.96; H, 7.96; N 3.66.

EXAMPLE 73

1-((N-Ethylamino)methyl-N-(2-(2-thienyl)ethyl))-5-methoxy tetralin hydrochloride Using the product (free base) of Example 15 and the procedures described in Examples 18 and 19 the desired compound was obtained, m.p. 149°–151° C. Anal. calcd. for $C_{20}H_{28}ClNOS$: C, 65.64; H, 7.71; H, 3.83. Found: C, 65.86; H, 8.00, N, 3.84.

EXAMPLE 74

6-Fluoro-1-aminomethyl-3,4-dihydronaphthalene hydrochloride

6-Fluorotetralone (8.2 g), and TMSCN (13.4 ml) in 15 ml benzene containing a trace of $AlCl_3$ or $ZnI_2$ was heated at 60°–65° C. for 6½ hrs. The reaction was added to $Et_2O$ (50 ml) then added dropwise to $Et_2O$ (350 ml) containing lithium aluminum hydride (3.8 g) under $N_2$. Upon complete addition, the mixture was gently refluxed for 5 hrs followed by stirring at room temperature overnight. The reaction was quenched by the successive addition of EtOAc (12 ml), $H_2O$ (4 ml), 15% aq. KOH (4 ml) and $H_2O$ (12 ml). After the quenching the mixture was stirred at room temperature for 1 hr, followed by the addition of anhydrous $Na_2SO_4$ with an additional ½ hr stirring. The reaction was filtered, ethereal HCl was added to the filtrate and the resulting precipitate filtered affording a product mp 177°–83° C. This was added to a isopropyl alcohol saturated with HCl (300 ml) and heated for 4½ hrs. The solution was cooled and evaporated to dryness and gave the desired compound, m.p. 200°–203° C.

EXAMPLE 75

6-Fluoro-1-aminomethyl-1,2,3,4-tetrahydronaphthalene hydrochloride

The product from Example 74 was reduced as in Example 2 but replacing the $NH_3$ with acetic acid and afforded the desired compound, m.p. 236°–38° C.

EXAMPLE 76

1-((N-Isopropylamino)methyl)-6-fluoro-tetralin hydrochloride

The product from Example 75 (1.5 g) was added to a solution of acetone (25 ml) and MeOH (25 ml) then 95% sodium cyanoborohydride (1.32 g) was added in portions. The pH of the reaction was adjusted to ca. pH 5 after complete addition of the $NaBH_3CN$. The reaction was then stirred at room temperature for 8 hrs. The reaction was evaporated to dryness, then dilute HCl and $CH_2Cl_2$ (50 ml) was added. The aqueous layer was separated, basified then $CH_2Cl_2$ added. The organic layer was separated, dried ($MgSO_4$), filtered and evaporated. The residue was taken up in $Et_2O$ (300 ml) then ethereal HCl added. The resulting precipitate was filtered and recrystallized from EtOAc/MeOH giving the desired compound, m.p. 212°–14° C.

EXAMPLE 77

1-((N-Isopropylamino)methyl-N-(2-(2-furyl)ethyl))-6-fluoro tetralin fumarate

The product (free base) of Example 76 was reacted as described in Examples 18 and 19 but replacing 2-thiopheneacetic acid with 2-furylacetic acid and gave the desired product after formation of the fumarate salt, m.p. 138°–39° C. Anal. calcd. for $C_{24}H_{30}FNO_5$: C, 66.80; H, 7.01; N, 3.25. Found: C, 66.36; H, 6.89; N, 3.20.

EXAMPLE 78

1-((N-Isopropylamino)methyl)-5-fluoro tetralin hydrochloride

Following the procedures described in Examples 74–76 but replacing 6-fluoro-1-tetralone with 5-fluoro 1 tetralone afforded the desired product.

EXAMPLE 79

1-((N-Isopropylamino)methyl-N (2-(2-furyl)ethyl))-5-fluoro tetralin methanesulfonate The product (free base) of Example 78 was treated as described in Examples 18 and 19 but replacing 2-thiopheneacetic acid with 2-furylacetic acid giving the desired compound.

EXAMPLE 80

1((N-Methylamino)methyl-N-(2-(1,4-benzodioxan-)ethyl))-6,8-dimethoxy tetralin hydrochloride Starting with 1-((N-methylamino)methyl)-6,8-dimethoxy tetralin and using the procedures described in examples 4 and 5 but replacing 2-thiopheneacetic acid with 1,4-benzodioxanacetic acid gave the desired product, m.p. 210°–13° C. Anal. calcd. for $C_{24}H_{32}ClNO_4$: C, 66.42; H, 7.43; N. 3.23. Found: C, 66.29; H, 7.37; N, 3.18.

EXAMPLE 81

1-((N-Methylamino)methyl-N-(3-phenylpropyl))-6-hydroxy tetralin hydrochloride

Using the product from Example 6j and the procedure of Example 10 gave the desired compound, m.p. 120°–122° C. Anal. calcd. for $C_{21}H_{29}ClNO.\frac{1}{2}$ $H_2O$: C, 71.07; H, 8.24; N, 3.95. Found: C, 70.86; H, 8.08; N, 3.80.

EXAMPLE 82

1-((N-Methylamino)methyl-N-(2-(m-hydroxyphenyl-)ethyl))-6-hydroxy tetralin hydrochloride Using the product from example 6k and the procedure described in Example 10 the desired compound was obtained as an amorphous solid. Anal. calcd. for $C_{20}H_{26}ClNO_2 \cdot 2H_2O$: C, 62.57; H, 7.88; N, 3.65. Found: C, 62.35; H, 7.26; N, 3.43.

EXAMPLE 83

1-((N-Methylamino)methyl-N-(2-(m-hydroxyphenyl-)ethyl))-6-methoxy tetralin hydrochloride Using the product from Example 3 and the procedure of Example 4 replacing the 2-thiopheneacetic acid with m-acetoxyphenylacetic acid gave the corresponding amide. Using this amide and the procedure described in Example 5 afforded the desired compound as an amorphous solid. Anal. calcd. for $C_{21}H_{28}ClNO_2 \cdot H_2OC$, 66.39; H, 7.96; N, 3.69. Found: C, 66.59; H, 7.71; N, 3.65.

EXAMPLE 84

1-((N-Methylamino)methyl-N-(2-(m-fluorophenyl)ethyl))5,6-dimethoxy tetralin hydrochloride The product was obtained (m.p. 200°–201° C.) using the procedures described in Examples 1–5 but replacing 6-methoxy-1-tetralone with 5,6-dimethoxy-1-tetralone and using 3-fluorophenylacetic acid in place of 2-thiopheneacetic acid, m.p. 200°–201° C. Anal. calcd. for $C_{22}H_{29}FClNO_2$: C, 67.08; H, 7.42; N, 3.56. Found: C, 66.69; H, 7.47; N, 3.47.

EXAMPLE 85

1-((N-Methylamino)methyl-N-(2-(m-fluorophenyl-)ethyl))-5,6-dihydroxy tetralin hydrochloride Using the product of Exmaple 84 and the procedures described in Examples 9 and 10, the desired compound was obtained, m.p. 158°–60° C. Anal. calcd. for $C_{20}H_{25}FClNO_2 \cdot H_2O$: C, 62.57; H, 7.09; N, 3.65. Found: C, 62.41; H, 6.59; N, 3.74.

EXAMPLE 86

1-((N-Methylamino)methyl-N-(2-(2-thienyl)ethyl))-5,6-dimethoxy tetralin hydrochloride Using the procedures described in Examples 1–5 but replacing 6-methoxy-1-tetralone with 5,6-dimethoxy-1-tetralone gave the product, m.p. 235°–6° C. Anal. calcd. for $C_{20}H_{28}ClNO_2S$: C, 62.89; H, 7.39; N, 3.67. Found: C, 62.88; H, 7.68; N, 3.67.

EXAMPLE 87

1-((N-Methylamino)methyl-N-(2-(2-thienyl)ethyl))-5,6-dihydroxy tetralin hydrochloride Using the product of Example 86 and the procedures described in Examples 9 and 10 the desired product was afforded Anal. calcd. for $C_{18}H_{24}ClNO_2S$: C, 61.09; H, 6.84; N, 3.96. Found: C, 61.00; H, 7.14; N, 3.65.

EXAMPLE 88

1-(N-Methylamino)methyl-N-(2-phenethyl)) tetralin hydrochloride

Using the procedures described in Examples 1–5 but replacing 6-methoxy-1-tetralone with 1-tetralone and replacing 2-thiopheneacetic acid with 2-phenylacetic acid gave the product, m.p. 207°–208° C. Anal. calcd. for $C_{20}H_{26}ClN$: C, 76.05; H, 8.30; N. 4.43. Found: C, 75.77; H, 8.67; N, 4.58.

EXAMPLE 89

1-(N-Methylamino)methyl-N-(2-(3-nitro-4-hydroxyphenyl)ethyl))-6-methoxy tetralin hydrochloride Using the procedures described in Examples 1–5 but replacing 2-thiopheneacetic acid with 4-acetoxy-3-nitrophenylacetic acid gave the desired product. Anal. calcd. for $C_{21}H_{30}Cl_2N_2O \cdot \frac{1}{2}$ $H_2O$: C, 59.71; H, 7.40; N, 6.63. Found: C, 59.59; H, 7.48; N, 6.51.

EXAMPLE 90

1-((N-Methylamino)methyl-N-(2-(3-amino-4-hydroxyphenyl)ethyl))-6-methoxy tetralin dihydrochloride The product from Example 89 was catalytically reduced as in Example 66 but replacing 5% Pd/C with 20% Pd/C and gave the desired compound, m.p. 188°–90° C. Anal. calcd. for $C_{21}H_{30}Cl_2N_2O_2 \cdot \frac{1}{2}$ 1/2 $H_2O$: C, 59.71; H, 7.40; N, 6.63. Found: C, 59.59; H, 7.48; N, 6.51.

EXAMPLE 91

6-Methoxy-1,2,3,4-tetrahydro-1-naphthylene carboxylic acid

A mixture of 1-cyano-6-methoxy-1,2,3,4-tetrahydronaphthalene (18.7 g; 0.1 mol), 45% aq. KOH solution (220 ml) and ethylene glycol (180 ml) was refluxed for 6 h. The reaction mixture was cooled to 0° C. and acidified with cold concentrated hydrochloric acid. The acidic solution was extracted with methylene chloride. The organic layer was washed with brine, separated dried (MgSO$_4$), filtered, and evaporated to afford ca. 20 g of an oily residue. Crystallization with ether/hexane afforded ca. 17.1 g (83%) of a white crystalline solid, m.p. 81°-82° C.

EXAMPLE 92

N-Methoxy-N-methyl-6-methoxy-1,2,3,4-tetrahydro-1-naphthylene carboxamide

The product of Example 91 (15 g) was dissolved in benzene (100 ml) and oxalyl chloride (15 ml) and refluxed 1 hr under N$_2$. The solvent was evaporated and the residue azeotroped with benzene (2×40 ml). The resulting acid chloride (18.4 g), and N,O-dimethylhydroxyl amine hydrochloride was dissolved in ethanol free chloroform (200 ml) and the solution cooled to 0° C, then pyridine (13.4 ml) was slowly added. The mixture was then stirred at room temperature for 1 h then evaporated to dryness. The residue was partitioned between brine and a 1:1 mixture of Et$_2$O and CH$_2$Cl$_2$. The organic layer was separated, dried (MgSO$_4$), filtered, and evaporated affording the desired product as an oil (98% yield).

EXAMPLE 93

1-(1,2,3,4-Tetrahydro-6-methoxy-1-naphthyl)ethan1-one

The product from example 92 (4.98 g) was dissolved in dry THF (100 ml) cooled to 0° C., then a solution of methylmagnesium Grignard (20 ml of a 2.9M ether solution) was added under N$_2$. The reaction was stirred at 0° C. for ½ hr then diluted with ether (100 ml) and poured onto a saturated solution of NH$_4$Cl. Methylene chloride was added (100 ml) and the organic layer separated, washed with brine, dried (MgSO$_4$), filtered and evaporated affording a viscous oil (95% yield).

EXAMPLE 94

2-(1,2,3,4-Tetrahydro-6-methoxy-1-naphthyl)pyrrolidine

The product from Example 92 (2.49 g) was dissolved in dry THF (50 ml) and cooled to 0° C. Then, an excess (3-4 equiv.) of 2,2,5,5-tetramethyl-1-aza-2,5-disilacyclopentane-1-propyl magnesium bromide was added and the reaction stirred at 0° C. warming to room temperature overnight. The reaction was cooled to 0° C. then 10% HCl in EtOH was slowly added, followed by stirring for 3 h at room temperature. The solvent was evaporated and the residue dissolved in methanol. The mixture was cooled to 0° C., then treated with an excess of NaBH$_4$ and the mixture stirred at room for 3 h. The solvent was stripped in vacuo and the residue partitioned between ether and H$_2$O. The acidic aqueous layer was made basic then extracted with methylene chloride. The organic extract was dried (MgSO$_4$ filtered and evaporated in vacuo and the product purified by column chromatography on silica gel eluting with 1:6 EtOH/CH$_2$Cl$_2$ containing NH$_4$OH affording 1.2 g of desired product.

EXAMPLE 95

N-(2-(2-Furyl)ethyl)-2-(1,2,3,4-tetrahydro-6-methoxy-1-naphthyl)pyrrolidine difumarate The product from Example 94 was reacted as described in Examples 18 and 19 but replacing 2-thiopheneacetic acid with 2-furylacetic acid and gave the desired product, m.p. 110°-111° C. Anal. calcd. for C$_{29}$H$_{37}$NO$_{10}$: C, 62.47; H, 6.33; N, 2.51 Found: C,62.90; H, 6.39; N, 2.55.

EXAMPLE 96

N-(2-(2-Thienyl)ethyl)-2-(1,2,3,4-tetrahydro-6-methoxy-1-naphthyl)pyrrolidine methanesulfonate The product from Example 94 was reacted as described in Examples 18 and 19 and afforded the desired product.

EXAMPLE 97

N-(2-(m-Fluorophenyl)ethyl)2-(1,2,3,4-tetrahydro-6-methoxy1-naphthyl) pyrrolidine methanesulfonate Using the product from Example 94 and the procedures of Examples 18 and 19, but replacing 2-thienylacetic acid with m-fluorophenylacetic acid gave the desired product.

EXAMPLE 98

1-(6-Methoxy1,2,3,4-tetrahydro-1-naphthyl)-N-ethyl-1-amino ethane

The product of Example 93 (2 g) was dissolved in anhydrous MeOH (20 ml) and EtNH$_2$ (3 ml) and the pH adjusted to ca. 8 with methanolic HCl. Sodium cyanoborohydride (500 mg) was added and an additional 2 ml methanolic HCl dropwise. The reaction was stirred under N$_2$ for 48h then 6 N HCl added to pH<2. The methanol was removed under vacuum and the aqueous layer extracted with CH$_2$Cl$_2$ (2×100 ml). The organic layer was separated, washed with brine, dried (MgSO$_4$), filtered and evaporated giving 0.18 g of an oil. The neutral CH$_2$Cl$_2$ extract was dried (MgSO$_4$), filtered and evaporated then partitioned between 2 N HCl and a mixture of ether/hexane. The organic layer was separated and discarded. The acidic layer was basified and extracted with CH$_2$Cl$_2$. The organic layer was separated, dried (MgSO$_4$), filtered and evaporated giving an additional 1.12 g of product.

EXAMPLE 99

1-(6-Methoxy-1,2,3,4-tetrahydro-1-naphthyl)-N-methyl-1-amino ethane

Using the procedure described in Example 98 but replacing EtNH$_2$ with methylamine afforded the desired product in 59% yield.

EXAMPLE 100

N-(2-Phenylethyl)-1-(6-methoxy-1,2,3,4-tetrahydro-1-naphthyl)-N-methyl-1-amino ethane hydrochloride Using the procedures described in Examples 4 and 5 but replacing the 2-thiopheneacetic acid with phenylacetic acid and the product from Example 99 gave the desired compound, m.p. 159°-160° C. Anal. calcd. for C$_{22}$H$_{30}$ClNO: C, 73.23; H, 8.32; N. 3.88. Found: C, 73.28; H, 8.28; N. 3.86.

EXAMPLE 101

N-(2-(Phenyl)ethyl)-1-(6-hydroxy-1,2,3,4-tetrahydro-1-nachthyl)-N-methyl-1-amino ethane hydrobromide Using the product from Example 100 and the procedure of Example 9 gave the desired product, m.p. 88°-90° C. Anal. calcd. for C$_{21}$H$_{28}$BrNO: C, 64.62; H, 7.18; N, 3.59. Found: C, 64.50; H, 7.14; N, 3.54.

EXAMPLE 102

N-(2-(2-Furyl)ethyl)-1-(6-methoxy-1,2,3,4-tetrahydro-1-naphthyl)-N-methyl-1-amino ethane methanesulfonate Using the product from Example 99 and the procedures described in Examples 18 and 19 but replacing 2-thiopheneacetic acid with 2-furylacetic acid gave the desired product, (M+H)+314.

EXAMPLE 103

N-(2-(2-Thienyl)ethyl)-1-(6-methoxy-1,2,3,4-tetrahydro-1-naphthyl)-N-methyl-1-amino ethane hydrochloride Using the product from Example 99 and the procedures described in Examples 4 and 5 g-ave the desired product, m.p. 160°-61° C. Anal. calcd. for $C_{20}H_{28}ClNOS$: C, 65.66; H, 7.66; N, 3.83. Found: C, 65.82; H, 7.74; N, 3.82.

EXAMPLE 104

N-(2-(2-Furyl)ethyl)-1-(6-methoxy-1,2,3,4--tetrahydro-1-naphthyl)-N-ethyl-1-amino ethane hydrochloride Using the compound from Example 98 and the procedures described in Examples 18 and 19 but replacing 2-thiopheneacetic acid with 2-furylacetic acid gave the desired product, (M+H)328. $^1H$ NMR ($CDCl_3$): 0.85(3H,d, J=8.0 Hz), 1.04 (3H, t, J=8.0 Hz), 1.32-1.47 (1H,m), 1.61-1.72 (1H,m), 1.75-1.88 (1H,m), 2.26-2.43 (2H,m), 2.5-2.92 (9H,m), 3.75 (3H,s), 6.1 (1H,dd,J=3.0, 0.6 Hz), 6.28 (1H,dd,J=3.0, 1.5 Hz), 6.61 (1H,d,J=3.0 Hz), 6.63 (1H,dd,J=9.0, 3.0 Hz), 7.0 (1H,d,J=8.0 Hz), 7.3 (1H,dd,J=1.5, 0.6 Hz).

EXAMPLE 105

1-(1,2,3,4-Tetrahydro-6-methoxy-1-naphthyl)propan-1-one

Using the product of Example 92 and the procedure of Example 93 but replacing methyl magnesium bromide with ethyl magnesium bromide gave the desired product.

EXAMPLE 106

1-(6-Methoxy-1,2,3,4-tetrahydro-1-naphthyl)-N-methyl-1-amino propane

Using the product of Example 105 with the procedure described in Example 98 but replacing the ethylamine with methylamine gave the desired product.

EXAMPLE 107

N-(2-(2-Furyl)ethyl)-1-(6-methoxy-1,2,3,4-tetrahydro-1-naphthyl)-N-methyl-1-amino propane hydrochloride Using the product from Example 106 and following the procedures described in Examples 18 and 19 but replacing 2-thiopheneacetic acid with 2-furylacetic acid gave the desired product. $^1H$ NMR ($CDCl_3$): 0.84-1.0 (5H,m); 1.4-1.9 (3H,m); 2.38 (3H,s); 2.5-2.95 (9H,m); 3.65 (3H,s); 6.1 (1H,dd,J=3.0,-0.6 Hz); 6.29 (1H,dd,J=3.0, 1.5 Hz); 6.59 (1H, d,J=3.0 Hz); 6.63 (1H,dd,J=9.0, 3.0 Hz); 6.90 (1H,d,J=9.0); 7.28 (1H,dd,J=1.5, 0.6 Hz).

EXAMPLE 108

N-(2-(m-Fluorophenyl)ethyl)-1-(6-methoxy-1,2,3,4-tetrahydro-1-naphthyl)-N-methyl-1-amino propane hydrochloride Using the product of Example 106 and the procedures described in Examples 4 and 5 but replacing 2-thiopheneacetic acid with m-fluorophenylacetic acid gave the desired product.

EXAMPLE 109

N-(2-(m-Fluorophenyl)ethyl)-1-(6-hydroxy-1,2,3,4-tetrahydro-1-naphthyl)-N-methyl-1-amino propane hydrobromide Using the product of Example 108 with the procedure of Example 9 gave the desired product.

EXAMPLE 110

N-(2-(m-Fluorophenyl)ethyl)-2-(1,2,3,4-tetrahydro-1-naphthyl-6-hydroxy) pyrrolidine hydrobromide Using the product from Example 97 and the procedure of Example 9 gave the desired product.

EXAMPLE 111

1-(N-Methylamino)methyl-N-(2-(2-thienyl)ethyl))-5-hydroxy tetralin hydrochloride 1-(N-methylamino)methyl-5-trimethylsilyoxy tetralin was reacted as in Example 18 and gave the desired amide. This amide was then treated as in Example 5 and afforded the desired compound, m.p. 202°-3° C. (free base).

EXAMPLE 112

6-Acetamido3,4-dihydronaphthylene-1-carbonitrile

Using the procedure of Example 1, but replacing 6-methoxy1-tetralone with 6-acetamido-1-tetralone gave the desired product.

EXAMPLE 113

6-Amino-(1,2,3,4-tetrahydro1-naphthylene) carboxylic acid

The product from Example 112 was reduced with $NaBH_4$ in MeOH and DME then hydrolyzed to the carboxylic acid as described in Example 92.

EXAMPLE 114

1-((N-Methylaminomethyl-N-(2-phenylethyl))-6-amino tetralin dihydrochloride

Replacing 2-thiopheneacetic acid with the product from Example 113 and using the procedure of Example 18 with N-methylphenethyl amine gave the desired amide. This amide was reduced as in Example 19 and gave the desired product, m.p. 255°-56° C. Anal. calcd. for $C_{20}H_{28}Cl_2N_2$: C, 72.59; H, 8.22; N. 8.46. Found: C, 72.42; H, 8.41; H, 8.39.

EXAMPLE 115

1-((N-Methylamino)methyl-N-(2-(2-thienyl)ethyl))-5-iodo-6-hydroxy tetralin hydrochloride The product from Example 7 (free base) was iodinated with silver trifluoroacetate in $CH_2Cl_2$ at 0° C., and afforded the desired compound.

EXAMPLE 116

1-((N-Methylamino)methyl-N-(2-phenylethyl))5-iodo-6-hydroxy tetralin hydrochloride The product from Example 11 (free base) was iodinated with chloramine-T and sodium iodide then treated with methanolic HCl to give the product, m.p. 112°–114° C.

EXAMPLE 117

1-((N-Methylamino)methyl-N-(2-phenylethyl))-5-iodo-6-amino tetralin dihydrochloride The product from Example 114 was reacted as described in the procedure of Example 116 and afforded the desired product.

EXAMPLE 118

1-((N-Methylamino)methyl-N-(3-(2-furyl)propyl))-6-methoxy tetralin hydrochloride The product from Example 3 was reacted with 2-furylpropionic acid using the procedure of Example 18. The resulting amide was reduced as described in Example 19 and afforded the desired compound, m.p. 140°–41° C. Anal. calcd. for $C_{20}H_{28}ClNO_2$ C, 66.33; H, 7.21; N, 4.55. Found: C, 66.27; H, 7.19; N, 4.53.

EXAMPLE 119

1-((N-Methylamino)methyl-N-(2-(m-methylphenyl)ethyl))-5-methoxy indane hydrochloride Using the procedures described in Examples 1–5 but replacing 6-methoxy-1-tetralone with 5-methoxy-1-indanone and replacing 2-thiopheneacetic acid with m-methylphenyl acetic acid gave the desired compound, m.p. 183°–84° C. Anal. calcd. for $C_{21}H_{28}ClNO \cdot H_2O$ C, 69.31; H, 8.31; N, 3.85. Found: C, 69.44; H, 7.93; N, 3.90.

EXAMPLE 120

6-Methoxy-1-(3-phenylpyrrolidino-1-carbonyl) tetralin

Using 3-phenylpyrrolidine and the procedure described in Example 4 but replacing 2-thiopheneacetic acid with the product of example 91 gave the desired amide.

EXAMPLE 121

6-Methoxy-1-(3-phenylpyrrolidino-1-methyl) tetralin hydrochloride

Reduction of the product of Example 120 using the procedure described in Example 17 gave the desired compound, m.p. 228°–232° C. Anal. calcd. for $C_{22}H_{28}ClNO$: C, 73.83; H, 7 89: N. 3.91 Found: C, 73.68; H, 7.86; N, 3.91.

EXAMPLE 122

2-(2-Thienylmethyl)pyrrolidine

Using the procedure of Example 92 but replacing the product of Example 91 with 2-thiopheneacetic acid gave a 90% yield of the desired carboxamide. This carboxamide was reacted as described in Example 94 and gave the desired product in 43% yield.

EXAMPLE 123

6-Methoxy-1-(2-(2-thienylmethyl)pyrrolidino-1-methyl) tetralin hydrochloride

The product of Example 122 was reacted as described in Example 4 but replacing 2-thiopheneacetic acid with the product of Example 91 gave the desired amide. This was reduced as described in Example 17 and afforded a foam, m.p. 85°–89° C. Anal. calcd. for $C_{21}H_{28}ClNOS \cdot \frac{1}{2} H_2O$: C, 65.18; H, 7.55; N. 3.62. Found: C, 65.06; H, 7.21; N, 3.82.

EXAMPLE 124

5-Methoxy-3-phenyl-1-tetralone o-Anisaldehyde (20.5 g) was treated with 1,3-propanedithiol (24 ml) in the presence of BF. etherate (4 ml) and $CH_2Cl_2$ (300 ml). This dithiane derivative (4.7 g) was reacted with n-BuLi (2.5 M hexane solution) (7.3 ml), methyl cinnamate (3.4 g) and 1,3-dimethyl-2-imidazolidone (4.6 ml) affording the desired product $(M+H)^+ 389$. Desulfurization was accomplished with Raney Nickel and EtOH, followed by hydrolysis to the desired carboxylic acid. Cyclization to the desired 5-methoxy-3-phenyl-1-tetralone was accomplished by heating with polyphosphoric acid, $(M+H)^+ 253$.

EXAMPLE 125

1-(N-Methylamino)methyl-N-(2-(2-thienyl)ethyl))-3-phenyl-5-methoxy tetralin hydrochloride The product from Example 124 was reacted as described in Examples 1–5 and gave the desired product, $(M+H)^+ 392$.

EXAMPLE 126

6-Methoxy-3-phenyl-1-tetralone

Using the procedure described in Example 124 but replacing o-anisaldehyde with m-anisaldehyde afforded the desired product, $(M+H)^+ 253$.

EXAMPLE 127

1-(N-Methylamino)methyl-N-(2-(2-thienyl)ethyl))-3-phenyl-6-methoxy tetralin hydrochloride The product from Example 126 was treated as described in Examples 1–5 and afforded the desired product, m.p. 155°–160° C. Anal. calcd. for $C_{25}H_{30}NOS$: C, 70.15; H, 7.06; N. 3.27. Found: C, 70.42; H, 7.19; N, 3.24.

EXAMPLE 128

1-((N-Methylamino)methyl-N-(2-(2-furyl)ethyl))-6-methoxy 7-methyl tetralin hydrochloride Using the procedures described in Examples 1–3 and Examples 18–19 but replacing-6-methoxy-1-tetralone with the product of Example 38 and replacing 2-thiopheneacetic acid with 2-furylacetic acid gave the desired compound, m.p. 188°–89C. Anal. calcd. for $C_{20}H_{28}ClNO_2$: C, 68.65; H, 8.07; N, 4.00. Found: C, 68.59; H, 8.20; N, 3.95.

EXAMPLE 129

1-((N-Methylamino)methyl-N-(2-(2-thienyl)ethyl))-5-chloro tetralin hydrochloride Using the procedures described in Examples 46–49 but replacing 6-chloro-1-tetralone with 5-chloro-1-tetralone afforded the desired product, m.p. 216°–217° C.

Anal. calcd. for $C_{18}H_{23}Cl_2NS$: C, 60.67; H, 6.18; N, 3.93. Found: C, 60.67; H, 5.57; N, 3.95.

EXAMPLE 130

6-Methoxy-3-methyl-1-tetralone

The compound was prepared as described in Example 124 replacing methyl cinnamate with ethyl crotonate affording the desired product, $(M+H)^+ 191$.

EXAMPLE 131

1-((N-Methylamino)methyl-N-(2-(2-thienyl)ethyl))-3-methyl-6-methoxy tetralin hydrochloride Using the procedures described in Examples 1-5 but replacing-6-methoxy-1-tetralone with the product of Example 130 gave the desired compound, $(M+H)^+ 330$.

EXAMPLE 132

Dimethyl (2-thienyl)methylidene malonate

A solution of 2-thiophene carboxaldehyde (20.0 g), dimethyl malonate (22.1 ml), acetic acid (2.0 ml) and piperidine (0.7 ml) in 130 ml of benzene was heated at reflux under azeotropic conditions. After 4 hours the reaction mixture was cooled to room temperature. diluted with $Et_2O$ (100 ml), washed with 5% HCl (50 ml), brine (50 ml). sat. $NaHCO_3$ (50 ml). dried ($MgSO_4$). filtered and concentrated in vacuo. Distillation of the resulting amber oil under reduced pressure afforded 39 g of the desired compound which crystallized upon standing, m.p. 44°-46° C.

EXAMPLE 133

3-Cyano-3-(2-thienyl) propionic acid

To a mechanically stirred solution of 12.4 g of Example 132 in 135 ml of abs. EtOH was added in one portion a solution of KCN (3.9 g) in 7.0 ml of water, and the mixture heated to 70° C. After 20 hr at 70° C., the reaction mixture was cooled to 15° C., filtered, and concentrated in vacuo. The residue was taken up into $Et_2O$ (150 ml) and 10% aq. KOH (100 ml). The layers were separated and the aqueous phase reextracted with $Et_2O$ (100 ml).

The organic extracts were combined, dried ($MgSO_4$), filtered and concentrated to afford an amber liquid. Bulb to bulb distillation under reduced pressure afforded 7.89 g of a pale yellow liquid which was carried on to the next reaction without further purification.

EXAMPLE 134

4-(2-Thienyl)-2-pyrrolidinone

To a suspension of 1.23 g of cobalt boride and 2.0 g of the product of Example 133 in 60 ml of absolute methanol was added 2.50 g of borane tert-butyl amine complex, and the reaction was heated to reflux. After 6 h at reflux, the reaction was cooled to room temperature, filtered and concentrated. The residue was taken up unto EtOAc (70 ml) and 5% aqueous HCl (25 ml). The phases were separated and the aqueous phase reextracted with EtOAc (50 ml). The extracts were combined, dried ($MgSO_4$), filtered and concentrated. Chromatography of the residue on silica gel (elution with EtOAc) afforded 0.775 g of product as a white, crystalline material, m.p. 75.0°-76.5° C. Anal. calcd. for $C_8H_9NOS$: C, 57.46; H, 5.42; N, 8.38. Found: C, 57.64; H, 5.58; N, 8.47.

EXAMPLE 135

3-(2-Thienyl)pyrrolidine

To a suspension of $LiAlH_4$ (0.46 g) in THF (25 ml) was added the product of Example 134 (1.0 g) in THF (30 ml). After the addition was complete the reaction was heated at reflux for 4 hrs.

The reaction was cooled to 0° C. and quenched by the dropwise addition of water (0.46 ml), 15% aq. KOH (0.46 ml), followed by another 1.4 ml of water. After 30 min., the reaction was filtered and concentrated. The residue was taken up into EtOAc (60 ml), washed thoroughly with 5% aq. HCl (2×30 ml). The aqueous phases were combined, basified with 15% aq. KOH to pH 10 and extracted with EtOAc (2×50 ml). The organic extracts were combined, dried ($MgSO_4$), filtered and concentrated. Bulb to bulb distillation under reduced pressure afforded the desired product, $(M+H)^+ 154$.

EXAMPLE 136

6-Methoxy-1-(3-(2-thienyl)pyrrolidino-1-methyl) tetralin hydrochloride

Using the products of Examples 91 and 135 and the procedures described in Examples 4 and 17, the desired compound was afforded, 114°-117° C. dec. Anal. calcd. for $C_{20}H_{26}ClNOS$: C, 66.00; H, 7.20; N, 3.85. Found: C, 65.68; H, 7.14; N, 3.79.

EXAMPLE 137

N-2-(2-furyl)ethyl)-2-(1,2,3,4-tetrahydro-6-hydroxy-1-naphthyl) pyrrolidine hydrobromide The product of Example 95 was reacted as described in Example 9 and gave the desired compound.

EXAMPLE 138

N-(2-(2-Furyl)ethyl)-2-(1,2,3,4-tetrahydro-6-methoxy-3-methyl-1-naphthyl) pyrroliding hydrochloride The product from Example 133 was reacted as described in Example 13 and then Examples 91 and 92. This product was treated as in Example 94 and then Examples 18 and 19, affording the desired compound.

EXAMPLE 139

N-(2-(2-Furyl)ethyl)-2-(1,2,3,4-tetrahydro-6-hydroxy-3-methyl-1-naphthyl) pyrrolidine hydrobromide The product of Example 138 was reacted as in Example 9 giving the compound.

EXAMPLE 140

N-(2-(2-Furyl)ethyl)-2-(1,2,3,4-tetrahydro-6-methoxy-3-phenyl-1-naphthyl) pyrrolidine hydrochloride The product of Example 126 was reacted as described in Example 13 and then Examples 91 and 92. This product was used as described in Example 94, followed by Examples 18 and 19, giving the desired compound.

EXAMPLE 141

1-((N-methylamino)methyl-N-(2-(2-furyl)ethyl))-6-methoxy-7-fluoro tetralin methanesulfonate Using the procedures described in Example 1 but replacing 6-methoxy-1-tetralone and $ZnI_2$ with 6-methoxy-7-fluoro tetralone and LiCN afforded the 1-cyano derivative. Catalytic reduction with Pd/C at 4 atm. gave the corresponding 1-aminomethyl tetralin derivative in 97% yield. Utilizing this product and the procedures in examples 16-19 gave the desired product, m.p. 115°-116° C. Anal. calcd.. for $C_{19}H_{24}NO_2F \cdot CH_3SO_3H$: C, 58.09; H, 6.82; N, 3.39. Found: C, 57.86; H, 6.84; N, 3.43.

EXAMPLE 142

1,2,3,4-Tetrahydro-5,6-methylenedioxy-1-naphthylene carboxylic acid

To a solution of 1-cyano-3,4-dihydro-5,6-methylenedioxynaphthlene (5.0 g) in ethanol (80 ml) was added in small portions sodium borohydride (1.44 g). After the addition was complete the reaction was heated to reflux. After 2 hours, the reaction was cooled and concentrated. The residue was taken up into 1 N HCl and $CH_2Cl_2$ and the layers separated. The organic phase was washed with water, brine, dried over $MgSO_4$, filtered and concentrated. The resulting material was dissolved into ethylene glycol (41 ml) treated with 45% KOH (30 ml) and heated to reflux. After 3 hours the reaction was cooled with an ice bath, diluted with ice/water and acidified with concentrated HCl, upon which a white precipitate formed. The product was extracted with ethyl acetate (3×75 ml), washed with brine, dried over $MgSO_4$, filtered and concentrated to afford the desired product, m.p. 165°-167° C.

EXAMPLE 143a 5,6-Methylenedioxy-1-(3-phenylpyrrolidino-1-methyl) tetralin methanesulfonate Using 3-phenylpyrrolidine and the procedures described in Examples 4 and 5 but replacing 2-thiopheneacetic acid with Example 142 afforded the desired compound, m.p. 123°-124° C. Anal. calcd. for $C_{22}H_{25}NO_2 \cdot CH_3SO_3H$: C, 64.01; H, 6.77; N. 3.25. Found: C, 63.97; H. 6.83; N. 3.22.

EXAMPLES 143b, 143c 5,6-Methylenedioxy-1R-(3R-phenylpyrrolidino-1-methyl) tetralin methanesulfonate and 5,6-Methylenedioxy-1R-(3S-phenylpyrrolidino-1-methyl) tetralin methanesulfonate The product of Example 143a was chromatographed on silica qel (elution with 20 % $ET_2O$/hexanes, saturated with $NH_3$) to provide the R,R/S,S diastereomer which was converted to the corresponding methane sulfonate derivative, m.p. 166°-168° C. Anal. calcd. for $C_{22}H_{25}NO_2 \cdot CH_3SO_3H$: C, 64.01; H, 6.77; N, 3.24. Found: C, 63.89; H, 6.74; N, 3.24. Further elution provided the R,S/S,R diastereomer which was converted to the corresponding methane sulfonate derivative, m.p. 161°-162° C. Anal. calcd. for $C_{22}H_{25}NO_2 \cdot CH_3SO_3H$: C, 64.01; H, 6.77; N, 3.24 Found: C, 63.84; H, 6.68; N, 3.21.

EXAMPLE 144

5,6-Methylenedioxy-1-(3-(2-thienyl)pyrrolidino-1-methyl) tetralin methanesulfonate Using Example 135 and the procedures described in Examples 4 and 5 but replacing 2-thiopheneacetic acid with Example 142 afforded the desired compound, m.p. 150°-151° C. Anal. calcd. for $C_{20}H_{23}NO_2S \cdot CH_3SO_3H$: C, 57.64; H, 6.22; N, 3.20. Found: C, 57.17; H, 6.16; N, 3.15.

EXAMPLE 145

1,2,3,4-Tetrahydro-5-methoxy-1-naphthylene carboxylic acid

Using the procedure described in Example 142 but replacing 1-cyano-3,4-dihydro-5,6-methylenedioxynaphthylene with 1-cyano-3,4-dihydro-5-methoxynaphthylene provided the desired product, m.p. 101°-102° C.

EXAMPLE 146

5-Methoxy1-(3-(2-thienyl)pyrrolidino-1-methyl) tetralin hydrochloride

Using Example 135 and the procedures described in Examples 4 and 5 but replacing 2-thiopheneacetic acid with Example 145 afforded the desired compound, m.p. >230° C. Anal calcd. for $C_{20}H_{25}NOS \cdot HCl$: C. 66.00; H, 7.20; N, 3.85. Found: C, 65.87; H, 7.19; N, 3.83.

EXAMPLE 147

6-Fluoro-1,2,3,4-tetrahydro-1-naphthylene carboxylic acid

Using the procedure described in Example 142 but replacing 1-cyano-3,4-dihydro-5,6-methylenedioxynaphthylene with 1-cyano-6-fluoro-3,4-dihydronaphthylene provided the desired product, m.p. 90°-91° C.

EXAMPLE 148

6-Fluoro-1-(3-phenylpyrrolidino-1-methyl) tetralin methanesulfonate

Using 3-phenylpyrrolidine and the procedures described in Examples 4 and 5 but replacing 2thiopheneacetic acid with Example 147 afforded the compound, m.p. 166°-167° C. Anal. calcd. for $C_{21}H_{24}FN \cdot CH_3SO_3H$: C, 65.16; H, 6.96; N, 3.45. Found: C, 64.98; H, 6.93; N, 3.42.

EXAMPLE 149

6-Fluoro-1-(3-(2-thienyl)pyrrolidino-1-methyl) tetralin methanesulfonate

Using Example 135 and the procedures described in Examples 4 and 5 but replacing 2-thiopheneacetic acid with Example 147 afforded the desired compound, m.p. 136°-137° C. Anal. calcd. for $C_{19}H_{24}FN \cdot CH_3SO_3H$: C. 58.37; H, 6.37; N. 3.40. Found: C, 58.22; H, 6.34; N. 3.35.

EXAMPLE 150

2,3-Dihydro-4-methoxy-1-indene carboxylic acid

Using the procedure described in Example 142 but replacing 1-cyano-3,4-dihydro-5,6-methylenedioxynaphthylene with 1-cyano-2,3-dihydro-5-methoxy-1-indene provided the desired product, m.p. 117°-118° C.

EXAMPLE 151

5-Methoxy1-(3-(2-thienyl)pyrrolidino-1-methyl) indane hydrochloride

Using Example 135 and the procedures described in Examples 4 and 5 but replacing 2-thiopheneacetic acid with Example 150 provided the desired compound, m.p. 202°-204° C. dec. Anal. calcd. for $C_{19}H_{23}NOS \cdot HCl$: C, 65.22; H, 6.91; N, 4.00. Found: C, 65.04; H, 6.92; N, 3.93.

EXAMPLE 152

5-Methoxy-1-(3-phenylpyrrolidino-1-methyl) indane hydrochloride

Using 3-phenylpyrrolidine and the procedures described in Examples 4 and 5 but replacing 2-thiopheneacetic acid with Example 150 provided the desired compound, m.p. 126°–130° C. dec. Anal. calcd. for $C_{22}H_{25}NO\cdot CH_3SO_3H$: C, 65.48; H, 7.24; N, 3.47. Found: C, 65.44; H, 7.31; N. 3.46.

EXAMPLE 153

5-Methoxy-1-(3-(m-fluorophenyl)pyrrolidino-1-methyl) indane hydrochloride

Using 3-(m-fluorophenyl)pyrrolidine and the procedures described in Examples 4 and 5 but replacing 2-thiopheneacetic acid with Example 150 provided the desired compound, m.p. 205°–207° C. dec. Anal. calcd. for $C_{21}H_{24}FNO\cdot HCl$: C, 69.70; H, 6.96; N, 3.87. Found: C, 69.54; H, 7.06; N, 3.83.

EXAMPLE 154

6-Amino-1,2,3,4-tetrahydro-1-naphthylene carboxylic acid hydrochloride

Using the procedure outlined in Example 1 but replacing 6-methoxy-1-tetralone with 6-acetamido-1-tetralone afforded the desired unsaturated nitrile. A suspension of the above nitrile (24 g) in 260 mL of a 1:1 mixture of ethanol and dimethoxyethyl ether was treated with small portions of sodium borohydride (15 g). After the addition was complete the reaction was heated at reflux for 20 hours. The reaction was cooled to room temperature, quenched by the dropwise addition of acetone and concentrated. The residue was taken up into saturated $NH_4Cl$ and $CH_2Cl_2$. The phases were separated and the aqueous phase reextracted with $CH_2Cl_2$. The organic extracts were combined, dried over magnesium sulfate, filtered and concentrated to provide the desired saturated nitrile.

The above nitrile was taken up into concentrated hydrochloric acid (160 ml) and heated at reflux for 5 hours. The reaction was cooled to 0° C. and the resulting precipitate collected and washed with a 10% ethanol/ether solution to provide the desired product.

EXAMPLE 15

1-((6-amino-1,2,3,4-tetrahydro-1-naphthalenyl)carbonyl)-3-phenylpyrrolidine

A mixture of Example 154 (2.3 g) and thionyl chloride (50 ml) were heated at reflux for 45 minutes. The reaction was concentrated and the residue was co-concentrated with toluene (3×50 ml). To a solution of 3-phenylpyrrolidine in $CH_2Cl_2$ (30 ml) containing triethylamine (4.2 ml) at 0° C., was added dropwise a solution of the above acid chloride in $CH_2Cl_2$ (30 ml). After 8 hours, the reaction was concentrated to afford a brown oil. The residue was taken up into a mixture of water and ethyl acetate. The layers were separated and the organic phase washed with 1 N NaOH, brine, dried over magnesium sulfate, filtered and concentrated. Chromatography (elution with 2% $CH_3OH/CH_2Cl_2$) on silica gel provided for 2.7 g of the desired product.

EXAMPLE 156

6-Amino-1-(3-phenylpyrrolidino-1-methyl) tetralin dihydrochloride

Using the procedure described in Example 19 but replacing Example 18 with Example 155 yielded the desired compound, m.p. >260° C. Anal. calcd. for $C_{21}H_{26}N_2\cdot 2HCl$: C, 66.49; H, 7.44; N, 7.38. Found: C, 65.81; H, 7.41; N. 7.21.

EXAMPLE 157

6-(N-methylamino)-1-(3-phenylpyrrolidino-1-methyl) tetralin dihydrochloride

Using the procedure outlined in Example 3 but replacing Example 2 with Example 155 provided the desired compound, m.p. 231° C. Anal. calcd. for $C_{22}H_{28}N_2\cdot 2HCl$: C, 67.17; H, 7.69; N, 7.12. Found: C, 66.97; H, 7.88; N,. 7.12.

EXAMPLE 158

8-fluoro-5,6,-methylenedioxy-1-tetralone

To a solution of 8-fluoro-5,6-dimethoxy-1-tetralone (3.0 g) in toluene (30 ml) was added in small portions aluminum chloride (9.0 g). After the addition was complete, the reaction was heated to 80° C. and after 30 min. cooled to room temperature. The reaction mixture was poured into concentrated HCl/ice and the product extracted with ethyl acetate. The organic layer was washed with 1 N HCl, brine, dried over $MgSO_4$, filtered and concentrated to afford 2.0 g of product. To a mechanically stirred suspension of this material in 1,3-dimethyl-3,4,5,6-tetrahydro-2-(1H)pyrimidinone (14 ml) was added cesium carbonate (4.7 g) followed by the addition of bromochloromethane (0.99 ml) and the resulting mixture heated to 70° C. with vigorous stirring. After 4.5 hours, the reaction was cooled and poured into water (50 ml). The product was extracted with ethyl acetate (2×50 ml) and the extracts were combined, dried over $MgSO_4$, filtered and concentrated. Chromatography of the residue on silica gel (elution with 25% EtOAc/hexanes) afforded the desired product, m.p. 174°–175° C. Anal. calcd. for $C_{11}H_9FO_3$: C, 63.46; H, 4.36. Found: C, 63.28; H, 4.42.

EXAMPLE 159

8-Fluoro-1,2,3,4-tetrahydro-5,6-methylenedioxy-2-naphthylene carboxylic acid

Using the procedure in Example 1, but replacing 6-methoxy-1-tetralone with Example 158 afforded the unsaturated nitrile. m.p. 140.5°–142.5° C. Anal. calcd. for $C_{12}H_8FNO_2$: C, 66.36; H, 3.71; N, 6.45. Found: C, 66.17; H, 3.81; N, 6.34. This material was subjected to the reaction conditions described in Example 142 to provide the desired material.

EXAMPLE 160

8-Fluoro-5,6-methylenedioxy-1-(3-phenylpyrrolidino1-methyl) tetralin hydrochloride Using 3-phenylpyrrolidine and the procedures described in Example 4 and 5 but replacing 2-thiopheneacetic acid with Example 159 afforded the desired compound. m.p. 169°–170° C. Anal. calcd. for $C_{22}H_{24}NO_2\cdot CH_3SO_3H$ : C, 61.45; H, 6.28; N, 3.12. Found: C, 61.52; H, 6.25; N, 2.99.

EXAMPLE 161

8-Fluoro-5,6-methylenedioxy-1-(3-(m-fluorophenyl)pyrrolidino-1-methyl) tetralin hydrochloride Using 3-(m-fluorophenyl)pyrrolidine and the procedures described in Example 4 and 5 but replacing 2-thiopheneacetic acid with Example 159 afforded the desired compound.

EXAMPLE 162

8-Fluoro-5,6-methylenedioxy-1-(3-(2-thienyl)pyrrolidino-1-methyl) tetralin hydrochloride Using Example 135 and the procedures described in Example 4 and 5 but replacing 2-thiopheneacetic acid with Example 159 afforded the desired compound.

EXAMPLE 163

5,6-Methylenedioxy-1-(3-(m-fluorophenyl)pyrrolidino-1-methyl) tetralin methanesulfonate Using 3 (m-fluorophenyl)pyrrolidine and the procedures described in Example 4 and 5 but replacing 2-thiopheneacetic acid with Example 142 afforded the desired compound, m.p. 177°–179° C. dec. Anal. calcd. for $C_{22}H_{24}FNO_2 \cdot CH_3SO_3H$ : C, 61.45; H, 6.28; N, 312. Found: C, 61.27; H, 6.32; N, 3.07.

EXAMPLE 164

1-(N-Ethylamino)methyl-N-(2-(2-thienyl)ethyl))-5,6-methylenedioxy tetralin hydrochloride The desired compound (m.p 163°–164° C.) was prepared using the procedures outlined in examples 1, 2, 15, 4 and 5, but replacing-6-methoxy-1-tetralone with 5,6-methylenedioxy-1-tetralone. Anal. calcd. for $C_{20}H_{25}NO_2S \cdot HCl$: C, 63.23; H. 6.90; N. 3.69. Found. C, 63.15; H,, 6.86; N, 3.64.

EXAMPLE 165

1-((N-Ethylamino)methyl-N-(2 m-fluorophenethyl))-5,6-methylenedioxy tetralin hydrochloride The desired compound (m.p. 131.5°–132.5° C.) was prepared using the procedures in Example 165, but replacing 2-thiopheneacetic acid with m-fluorophenylacetic acid. Anal calcd. for $C_{22}H_{26}FNO_2 \cdot HCl$: C, 67.42; H, 6.94; N, 3.57. Found: C, 67.40; H, 6.98; N, 3.51.

EXAMPLE 166

1-((N-Methylamino)methyl-N-(2-m-fluorophenethyl))-5,6-methylenedioxy tetralin methanesulfonate Using the procedures in Example 23, but replacing 2-thiopheneacetic acid with m-fluoroacetic acid provided the desired product upon formation of the methanesulfonate salt, m.p. 144°–147° C. Anal. calcd. for $C_{21}H_{24}FNO_2 \cdot CH_3SO_3H$: C, 60.39; H, 6.45; N, 3.20. Found: C, 60.39; H. 6.48; N. 3.23.

EXAMPLE 167

1-((N-Methylamino)methyl N-(2-m-fluorophenethyl))-5,6-ethylenedioxy tetralin methanesulfonate The product was prepared (m.p. 174.175° C.) using the procedures in Example 30, but replacing 2-thiopheneacetic acid with m-fluorophenylacetic acid and formation of the methanesulfonate salt. Anal. calcd. for $C_{22}H_{26}FNO_2 \cdot CH_3SO_3H$: C, 61.18; H. 6.70; N, 3.10. Found: C, 60.94; H, 6.71; N, 3.09.

EXAMPLE 168

1-((N-Ethylamino)methyl N-(2-(2-thienyl)ethyl))-5,6-ethylenedioxy tetralin hydrochloride Using the procedures outlined in Example 164, but replacing 5,6-methylenedioxy 1-tetralone with 5,6-ethylenedioxy-1-tetralone provided the desired product. Anal. calcd. for $C_{21}H_{27}NO_2S \cdot HCl \cdot \frac{1}{2}H_2O$: C, 62.59; H. 7.25; N. 3.48. Found: C, 62.50; H, 6.95; N, 3.55.

EXAMPLE 169

1,2,3,4-Tetrahydro-5,6-ethylenedioxy-1-naphthylene carboxylic acid

Using the procedure in Example 142 but replacing 1-cyano-3,4-dihydro-5,6-methylenedioxy naphthylene with 1-cyano-3,4-dihydro-5,6-ethylene dioxynaphthylene provided the desired material.

EXAMPLE 170

5,6-Ethylenedioxy-1-(3-phenylpyrrolidino-1-methyl) tetralin hydrochloride

Using 3-phenylpyrrolidine and the procedures described in Examples 4 and 5 but replacing thiopheneacetic acid with Example 169 afforded the desired compound.

EXAMPLE 171

5,6-Ethylenedioxy-1-(3-(m-fluorophenyl)pyrrolidino 1-methyl) tetralin hydrochloride Using 3-(m-fluorophenyl)pyrrolidine and the procedures described in Examples 4 and 5 but replacing 2-thiopheneacetic acid with Example 169 afforded the desired compound.

EXAMPLE 172

5,6-Ethylenedioxy-1-(3-(2-thienyl)pyrrolidino-1-methyl) tetralin hydrochloride

Using 3-(2-thienyl)pyrrolidine and the procedures described in Examples 4 and 5 but replacing 2-thiopheneacetic acid with Example 169 afforded the desired compound.

EXAMPLE 173a & b (−)-5,6-Methylenedioxy-1R*-(3R*-phenylpyrrolidino-1-methyl) tetralin methanesulfonate and (−)-5,6-phenylpyrrolidino-1S*-(3R*-phenylpyrrolidino-1-methyl) tetralin hydrochloride Using (−)-3R*-phenylpyrrolidine and the procedures described in Examples 4 and 5 but replacing 2-thiopheneacetic acid with the product of Example 142 afforded a mixture of enantiomerically pure diastereomers. Chromatography on silica gel (elution with 20 % $Et_2O$/ Hexanes, saturated with $NH_3$) provided Example 173a (R,R) after conversion to the corresponding methane sulfonate salt, $[\alpha]_D + 29.73°$ (c 0.555, $CH_3OH$); $[\alpha]_D + 37.59°$ (c 0.580, $H_2O$). Anal. calcd. for $C_{22}H_{25}NO_2 \cdot CH_3SO_3H$: C, 64.01; H, 6.77; N, 3.24. Found: C, 63.96; H, 6.79; N, 3.25. Further elution provided Example 173b (R,S) which was converted to the corresponding hydrochloride salt, $[\alpha]_D - 19.07°$ (c 0.535, $CH_3OH$). Overlapping fractions were resubmitted under the above conditions for rechromatography.

EXAMPLE 174a & b (−)-5,6-Methylenedioxy-1S*-(3S*-phenylpyrrolidino-1-methyl) tetralin methanesulfonate and (+)-5,6-Methylenedioxy-1R*-(3S*-phenylpyrrolidino-1-methyl) tetralin hydrochloride Using (+)-3S*-phenylpyrrolidine and the procedures described in Examples 4 and 5 but replacing 2-thiopheneacetic acid with the product of Example 142 afforded a mixture of enantiomerically pure diastereomers. Chromatography on silica gel (elution with 20 % $Et_2O$/ Hexanes, saturated with $NH_3$) provided Example 174a (S,S) after conversion to the corresponding methane sulfonate salt, $[\alpha]_D$ −29.38° (c 0.565, $CH_3OH$); $[\alpha]_D$ −37.11° (c 0.617, $H_2O$). Anal. calcd. for $C_{22}H_{25}NO_2 \cdot CH_3SO_3H$: C, 64.01; H, 6.77; N, 3.24. Found: C, 63.97; H, 6.80; N, 3.21. Further elution provided Example 174b (S,R) which was converted to the corresponding hydrochloride salt, $[\alpha]_D$ +19.02° (c 0.510, $CH_3OH$). Overlapping fractions were resubmitted under the above conditions for rechromatography.

EXAMPLE 175

3-(o-Fluoro)phenylpyrrolidine

Using the procedures described in Example 132 and 133 but replacing 2-thiophene carboxaldehyde with o-fluorobenzaldehyde provided the ethyl 3-cyano-3-(o-fluoro)phenylpropionate. Reduction of the nitrile and cyclization was accomplished with Raney-Nickel in absolute ethanol at 60° C. under 4 atm of hydrogen, to provide the desired pyrrolidinone. Reduction as described in Example 135 provided the desired product.

EXAMPLE 176a 5,6-Methylenedioxy-1-(3-(o-fluorophenyl)pyrrolidino-1-methyl) tetralin methanesulfonate Using the product of Example 175 and the procedures described in Example 4 and 5 but replacing 2-thiopheneacetic acid with the product of Example 142 afforded the desired compound, m.p. 169°-170° C. Anal calcd. for $C_{22}H_{24}FNO_2 \cdot CH_3SO_3H$: C, 61.45; H, 6.28; N, 3.12. Found: C, 61.52; H, 6.25; N, 2.99.

EXAMPLE 176b & c 5,6-Methylenedioxy-1R-(3R-(o-fluorophenyl)pyrrolidino-1-methyl) tetralin methanesulfonate and 5,6-Methylenedioxy-1R-(3S-(m-fluorophenyl)pyrrolidino-1-methyl) tetralin methanesulfonate Using the procedure described in Example 143a & b, chromatography of the product of Example 176a provided the R,R/S,S diastereomer Example 176b, m.p. 186°-187° C. (Anal. calcd. for $C_{22}H_{24}FNO_2 \cdot CH_3SO_3H$: C, 61.45; H, 6.28; N, 3.12. Found: C, 61.17; H, 6.26; N, 3.06) and the R,S/S,R diastereomer, Example 176c, m.p. 160°-162° C. (Anal. calcd. for $C_{22}H_{24}FNO_2 \cdot CH_3SO_3H$: C, 61.45; H, 6.28; N, 3.12. Found: C, 61.50; H, 6.20; N, 3.07).

EXAMPLE 177

5,6-Dihydroxy-1-tetralone

To a solution 5,6-dimethoxy-1-tetralone (100 g) in toluene (958 ml) was added aluminum chloride (200 g) in small portions. After the addition was complete the reaction was heated to 80° C. and mechanically stirred for 2 hours. The reaction was cooled and slowly poured into ice and concentrated HCl. The resulting solids were filtered and washed with cold dilute HCl. The resulting solids were taken up into monoglyme, dried ($MgSO_4$), filtered, treated with charcoal, refiltered and concentrated. The residue was co-concentrated with acetonitrile to provide upon cooling 82.5 g of desired product as an off white solid, m.p. 191°-194° C.

EXAMPLE 178

5,6-Methylenedioxy-1-tetralone

To a solution of the product of Example 177 (30 g) in DMF (390 ml) was added cesium carbonate (83 g) followed by bromochloromethane (33 g) and the resulting mixture heated to 100° C. and mechanically stirred for 2 hours. The reaction was cooled, filtered and the solids washed with ethyl acetate. The filtrate concentrated and the residue taken up into water and toluene. The layers were separate and the aqueous layer reextracted with toluene. The extracts were combined, dried ($MgSO_4$), filtered, treated with charcoal, refiltered and concentrated to provide 29.9 g of the desired product, m.p. 132°-136° C.

EXAMPLE 179

5-Benzyloxy-6-methoxy-1-tetralone

A mixture of the product of Example 177 (8.3 g), powdered potassium carbonate (10.1 g), powdered potassium bicarbonate (4.6 g) and benzyl bromide (5.5 ml) in acetone (81 ml) was mechanically stirred at reflux for 3 hours. The reaction was cooled, filtered and the solids washed with acetone. The filtrate was concentrated and the residue taken up into ethyl acetate, washed with 0.5 N HCl, brine, dried ($MgSO_4$), filtered and concentrated. Chromatography on silica gel (elution with 30% $Et_2O$/Hexanes) provided 5.3 g of desired 5-benzyloxy derivative and 4.3 g of recovered starting material after rechromatography of overlapping fractions.

A mixture of the above material (5.3 g), potassium hydroxide (1.2 g) and methyl iodide (3.1 ml) in abs. ethanol (48 ml) was heated at reflux for 6 hours. The reaction was cooled and concentrated. To the resulting residue was added water and the product extracted out with ethyl acetate (3x). The extracts were combined, washed with water, brine, dried ($MgSO_4$), filtered and concentrated to provide 5.58 g of desired material, m.p. 64°-64° C.

EXAMPLE 180

5-Hydroxy-6-methoxy-1-(3-phenylpyrrolidino-1-methyl) tetralin hydrochloride

To a solution of the product of Example 179 (3.62 g) in THF (13.2 ml) was added trimethylsilylcyanide (2.2 ml) followed by the addition of lithium cyanide (4.4 ml, 0.5 M in DMF). After 3 hours at room temperature, the reaction was concentrated and the residue partitioned between water and $Et_2O$. The layers were separated and the aqueous phase reextracted with $Et_2O$ (2x). The extracts were combined, washed with water, brine, dried ($MgSO_4$), filtered and concentrated to yield an orange oil. This material was dissolved into i-propanol (20 ml) and cooled to 0° C. After adding i-propanol saturated with HCl (20 ml), the reaction was stirred for 4 hours. The reaction was diluted with water (10 ml) the solid collected and dried under vacuum to provide 2.08 g of the unsaturated nitrile derivative. An addition 0.87 g of product could be obtained from the filtrate.

Using the procedures outlined in Examples 142 and 143, the 6-benzyloxy derivative was obtained. This material upon treatment with palladium hydroxide in methanol under 1 atm of hydrogen provided the desired material after conversion to the corresponding HCl salt, m.p. 199°–201° C. Anal. calcd. for $C_{22}H_{27}NO_2 \cdot HCl$: C, 70.67; H, 7.55; N, 3.75. Found: C, 70.92; H, 7.58; N, 3.70.

EXAMPLE 181

5-Benzyloxy-6-methoxy-1-tetralone

To a suspension of aluminum chloride (25.8 g) in methylene chloride (120 ml) was added 5,6-dimethoxy-1-tetralone (10.0 g) and the resulting mixture heated at reflux for 2.5 hours. The reaction was cooled and pored into ice/con. HCl and diluted with methylene chloride. The phases were separated and the aqueous phase reextracted with methylene chloride. The extracts were combined washed with 1 N HCl, brine, dried ($MgSO_4$), filtered and concentrated to provide 4.5 g of the 6-methoxy derivative.

The above material (4.4 g) and potassium hydroxide (1.6 g) in abs. ethanol (150 ml) was heated to reflux. To this mixture was added dropwise benzyl bromide (3.3 ml and the reaction allowed to start reflux for 3 hours. The reaction was concentrated, water added and the product extracted with ethyl acetate (2x). The extracts were combined washed with 1 N NaOH, brine, dried ($MgSO_4$), filtered and concentrated to provide 5.33 g of desired product.

EXAMPLE 182

5-Hydroxy-6-methoxy-1-(3-phenylpyrrolidino-1-methyl) tetralin hydrochloride

Using the procedures in Example 180 but replacing the product of Example 179 with the product of Example 181, provided the desired compound, m.p. 214°–215° C. Anal. calcd. for $C_{22}N_{27}NO_2 \cdot HCl$: C, 70.67; H, 7.55; N, 3.75. Found: C, 70.39; H, 7.41; N, 3.69.

EXAMPLE 183

5,6-Methylenedioxy-1-(3-(p-fluorophenyl)pyrrolidino-1-methyl) tetralin methanesulfonate Using 3-(p-fluorophenyl)pyrrolidine (prepared from p-fluorobenzaldehyde utilizing the procedures described in Example 175) and the procedures described in Example 4 and 5 but replacing 2-thiopheneacetic acid with the product of Example 142 afforded the desired compound, m.p. 177°–179° C. Anal. calcd. for $C_{22}H_{24}FNO_2 \cdot CH_3SO_3H$: C, 61.45; H, 6.28N, 3.12. Found: C, 61.51; H, 6.58; N, 3.00.

EXAMPLE 184

5,6-Methylenedioxy-1-(3-(m-methoxyphenyl)pyrrolidino-1-methyl) tetralin hydrochloride Using 3-(m-methoxyphenyl)pyrrolidine (prepared from m-methoxybenzaldehyde utilizing the procedures described in Example 175) and the procedures described in Example 4 and 5 but replacing 2-thiopheneacetic acid with the product of Example 142 afforded the desired compound, m.p. 212°–213° C. Anal. calcd. for $C_{23}H_{27}NO_3 \cdot HCl$: C, 68.73; H, 7.02N, 7.02, N, 3.48. Found: C, 68.231; H, 7.09; N, 3.46.

EXAMPLE 185

5,6-Methylenedioxy-1-(3-(o-methoxyphenyl)-pyrrolidino-1-methyl) tetralin hydrochloride Using 3-(o-methoxyphenyl)pyrrolidine (prepared from o-methoxybenzaldehyde utilizing the procedures described in Example 175) and the procedures described in Example 4 and 5 but replacing 2-thiopheneacetic acid with the product of Example 142 afforded the desired compound, m.p. 179°–180° C. Anal. calcd. for $C_{23}H_{27}NO_3 \cdot HCl \cdot \frac{1}{4}H_2O$: C, 67.97; H, 7.07; N, 3.45. Found: C, 67.64; H, 6.94; N, 3.43.

EXAMPLE 186

5,6-Methylenedioxy-1-(3-(p-methoxyphenyl)-pyrrolidino-1-methyl) tetralin hydrochloride Using 3-(p-methoxyphenyl)pyrrolidine (prepared from p-methoxybenzaldehyde utilizing the procedures described in Example 175) and the procedures described in Example 4 and 5 but replacing 2-thiopheneacetic acid with the product of Example 142 afforded the desired compound, m.p. 152°–153° C. Anal. calcd. for $C_{23}H_{27}NO_3 \cdot CH_3SO_3H$: C, 62.45; H, 6.77; N, 3.04. Found: C, 62.23; H, 6.71; N, 2.99.

EXAMPLE 187

5-Methoxy-1-(3-phenylpyrrolidino-1-methyl) tetralin methane sulfonate

Using 3-phenylpyrrolidine and the procedures described in Examples 4 and 5 but replacing 2-thiopheneacetic acid with the product of Example 145 afforded the desired compound, m.p. 158°–159° C. Anal. calcd. for $C_{22}H_{27}NO \cdot HCl \cdot \frac{1}{2}H_2O$: C, 64.76; H, 7.56; N, 3.28. Found: C, 64.98; H, 7.40; N, 3.30.

EXAMPLE 188

6-(N-N'-dimethylamino)-1-(3-phenylpyrrolidino-1-methyl)tetralin dihydrochloride A suspension of 10% Pd/C (0.75 g) and Example 155 in abs. methanol (245 ml) containing formalin (5 ml) was stirred and room temperature under 4 atm. of hydrogen. The reaction was filtered upon completion and concentrated. The residue was taken up into ethyl acetate, washed with brine, dried ($MgSO_4$), filtered and concentrated. Chromatography on silica gel (elution with 1% EtOH/EtOAc) provided the N-N-dimethylamino derivative, which was subjected under the conditions described in Example 5 to provide the desired product, m.p. 205°–206° C. Anal. calcd. for $C_{22}H_{30}N_2 \cdot 2$ HCl: C, 67.80; H, 7.92; N, 6.88. Found: C, 67.27; H, 7.86; N, 6.80.

EXAMPLE 189

6-Methylsulfonamido-1-tetralone

A mixture of 6-acetamido-1-tetralone (50 g) and 6 N HCl (400 ml) was heated at reflux for 2 hours, cooled and extracted with $Et_2O$. The aqueous phase was basified with ammonium hydroxide upon which a precipitate formed. The solid was collected, dried under vacuum and chromatographed on silica gel (elution with $CH_2Cl_2$ followed by 1% $CH_3OH/CH_2Cl_2$) to provide 22.1 g of the amino derivative.

To a solution of the above amino derivative (7.0 g) in pyridine (40 ml) at 0° C. was added dropwise methanesulfonyl chloride (3.7 ml) and the resulting mixture allowed to stir at 0° C. for 45 minutes. The reaction was then warmed to room temperature and allowed to stir for 30 minutes. The reaction was poured into ice/con. HCl, upon which a precipitate formed. The solid was collected to afford 9.11 g of the desired compound.

EXAMPLE 190

6-Methylsulfonamido-1,2,3,4-tetrahydro-1-naphthylene carboxylic acid

Reaction of the product of Example 189 under the conditions described in Examples 1 and 142 provided the desired product.

EXAMPLE 191

6-Methylsulfonamido-1-(3-phenylpyrrolidino-1-methyl) tetralin hydrochloride

A mixture of the product of Example 190 (1.7 g) in thionyl chloride (30 ml) was heated at reflux for 1 hour. The was cooled, concentrated and co-concentrated with toluene. To a solution of the resulting acid chloride in methylene chloride (30 ml) was added dropwise a solution of 3-phenylpyrrolidine (1.02 g) in methylene chloride (10 ml) containing triethylamine (2.6 ml) at 5° C. After 1 hour at 5° C., the reaction was allowed to warm to room temperature and stir overnight. The reaction was concentrated, diluted with water and extracted with methylene chloride (2x). The extracts were combined, washed with 1 N NaOH, 1 N HCl, brine, dried (MgSO$_4$), filtered and concentrated. Chromatography of the residue on silica gel (elution with b 2% CH$_3$OH/CH$_2$Cl$_2$) afforded 1.84 g of material which was subjected to the conditions outlined in Example 5 to provide 0.8 g of the desired product, m.p. 139°–142° C. Anal. calcd. for C$_{22}$H$_{28}$N$_2$O$_2$S·HCl: C, 62.77; H, 6.94; N, 6.65. Found: C, 62.40; H, 7.04; N, 6.56.

EXAMPLE 192

6-(N-Methyl methylsulfonamido)-1-tetralone

To a suspension of sodium hydride (1.17 g) in DMF (50 ml) at 0° C. was added the product of Example 189 (9.0 g) in DMF (50 ml) and the resulting mixture allowed to stir for 30 minutes. The reaction was then treated with methyl iodide (2.5 ml) and allowed to stir at room temperature over night. The reaction was poured into ice water upon which a solid precipitated. The solid was collected, washed with water and Et$_2$O to provide 8.0 g of the desired material.

EXAMPLE 193

6-(N-methyl methylsulfonamido)-1-(3-(phenylpyrrolidino-1-methyl) tetralin hydrochloride Using the procedures outlined in Examples 1, 142 and 190 with the product of Example 192, provided the desired material, m.p. 195°–197° C. Anal. calcd. for C$_{23}$H$_{30}$N$_2$O$_2$S·Hcl: C, 63.50; H, 7.18; N, 6.44. Found: C, 63.42; H, 7.13; N, 6.41.

EXAMPLE 194

5.6-Ethylenedioxy-1-(3-(o-fluorophenyl)pyrrolidino-1-methyl) tetralin hydrochloride Using 3-(o-fluorophenyl)pyrrolidine and the procedures described in Examples 4 and 5 but replacing 2-thiopheneacetic acid with the product of Example 169 afforded the desired compound.

EXAMPLE 195

1,2,3,4-Tetrahydro-5,6-methylenedioxy-8-methyl-1-naphthylene carboxylic acid

Commencing with 5,6-dimethoxy-8-methyl-1-tetralone, the desired material was obtained following the conditions described in Examples 177, 178, 1 and 142.

EXAMPLE 196

5,6-Methylenedioxy-8-methyl-1-(3-phenylpyrrolidino-1-methyl) tetralin hydrochloride Using 3-phenylpyrrolidine and the procedures described in Examples 4 and 5 but replacing 2-thiopheneacetic acid with the product of Example 194 afforded the desired compound.

EXAMPLE 197

5,6-Methylenedioxy-8-methyl-1-(3-(o-fluorophenyl) pyrrolidino-1-methyl) tetralin hydrochloride Using 3-(o-fluorophenyl)pyrrolidine and the procedures described in Examples 4 and 5 but replacing 2-thiopheneacetic acid with the product of Example 195 afforded the desired compound.

EXAMPLE 198

5.6-Methylenedioxy-1-(3-(3,4-methylenedioxyphenyl) pyrrolidino-1-methyl) tetralin hydrochloride Using 3-(3,4-methylenedioxyphenyl)pyrrolidine (prepared from piperonal utilizing the procedures described in Example 175) and the procedures described in Examples 4 and 5 but replacing 2-thiopheneacetic acid with the product of Example 142 afforded the desired compound.

EXAMPLE 200

5,6Methylenedioxy-1-(3-(2,3-methylenedioxyphenyl) pyrrolidino-1-methyl) tetralin hydrochloride Using 3-(2,3-methylenedioxyphenyl)pyrrolidine (prepared from 2,3-methylenedioxybenzaldehyde utilizing the procedures described in Example 175) and the procedures described in Examples 4 and 5 but replacing 2-thiopheneacetic acid with the product of Example 142 afforded the desired compound.

EXAMPLE 201

5,6Methylenedioxy-1-(3-(o-methylphenyl1) pyrrolidino-1-methyl) tetralin hydrochloride Using 3-(o-methylphenyl)pyrrolidine (prepared from o-tolualdehyde utilizing the procedures described in Example 175) and the procedures described in Examples 4 and 5 but replacing 2-thiopheneacetic acid with the product of Example 142 afforded the desired compound.

EXAMPLE 201

5,6-Methylenedioxy-8-fluoro 1-(3-(o-methylphenyl) pyrrolidino-1-methyl) tetralin hydrochloride Using 3-(o-methylphenyl)pyrrolidine (prepared from o-tolualdehyde utilizing the procedures described in Example 175) and the procedures described in Examples 4 and 5 but replacing 2-thiopheneacetic acid with the product of Example 159 afforded the desired compound.

EXAMPLE 202

5,6-Methylenedioxy-8-methyl-1-(3-(o-methylphenyl) pyrrolidino-1-methyl) tetralin hydrochloride Using 3-(o-methylphenyl)pyrrolidine (prepared from o-tolualdehyde utilizing the procedures described in Example 175) and the procedures described in Examples 4 and 5 but replacing 2-thiopheneacetic acid with the product of Example 195 afforded the desired compound.

EXAMPLE 203

6-Methylenedioxy-8-fluoro-1-(3-(o-fluorophenyl) pyrrolidino-1-methyl) tetralin hydrochloride Using the product of Example 175 and the procedures described in Examples 4 and 5 but replacing 2-thiopheneacetic acid with the product of Example 159 afforded the desired compound.

The compounds were assessed for alpha-adrenergic receptor subtype selectivity by use of radioligand binding techniques as described previously (DeBernardis et.al. J. Med. Chem. 28, 1398 (1985)). Affinity for the alpha-1-receptor was assessed using rat liver homogenates and the radioligand [$^3$H]-prazosin; whereas for the alpha-2-receptor, rat cerebral cortices and the radioligand [$^3$H]-rauwolscine were utilized. Results obtained from the binding studies are shown in Table 1 for a representative sample of compounds disclosed herein, showing clearly the excellent affinity for the alpha-2-receptor, as well as the high degree of selectivity relative to the alpha-1-adrenoceptor.

TABLE 1

Radioligand Binding Data at alpha-1 and alpha-2 Adrenoceptors for Representative Compounds

| Example # | $K_i$ (nM) alpha 1 | $K_i$ (nM) alpha 2 | alpha-2 - Selectivity $K_i$ alpha-1/$K_i$ alpha 2 |
|---|---|---|---|
| 5 | 580 | 0.8 | 725 |
| 6b | 1180 | 5.0 | 236 |
| 6d | 500 | 1.5 | 333 |
| 6f | 2160 | 6.5 | 332 |
| 6h | 1505 | 3.5 | 430 |
| 7 | 565 | 1.6 | 353 |
| 11 (HCl salt) | 254 | 1.7 | 149 |
| 12 | 1208 | 5.0 | 242 |
| 22 | 695 | 1.3 | 535 |
| 23 | 445 | 1.7 | 262 |
| 26 | 175 | 0.6 | 292 |
| 27 | 525 | 2.0 | 263 |
| 30 | 470 | 4.0 | 118 |
| 34 | 330 | 2.6 | 127 |
| 36 | 655 | 6.9 | 95 |
| 37 | 645 | 3.7 | 174 |
| 41 | 950 | 2.9 | 326 |
| 42 | 1050 | 6.6 | 159 |
| 43 | 1400 | 6.0 | 233 |
| 44 | 590 | 5.6 | 105 |
| 49 | 1125 | 10.0 | 113 |
| 58 | 1830 | 18.0 | 102 |
| 67 | 1170 | 6.0 | 195 |
| 68 | 1175 | 6.0 | 196 |
| 69 | 1275 | 13.0 | 98 |
| 70 | 525 | 5.0 | 105 |
| 82 | 495 | 4.0 | 124 |
| 83 | 955 | 8.0 | 119 |
| 85 | 260 | 1.5 | 173 |
| 86 | 495 | 3.0 | 165 |
| 87 | 444 | 1.6 | 278 |
| 88 | 315 | 2.0 | 158 |
| 114 | 725 | 5.7 | 127 |
| 115 | 530 | 3.0 | 177 |
| 121 | 95 | 1.0 | 95 |
| 128 | 855 | 8.0 | 107 |
| 129 | 198 | 3.6 | 55 |
| 141 | 880 | 4.8 | 183 |
| 143a | 51 | 1.2 | 43 |
| 144 | 245 | 1.2 | 204 |
| 146 | 170 | 4.9 | 35 |
| 148 | 126 | 6.5 | 19 |
| 149 | 220 | 4.9 | 45 |
| 151 | 177 | 2.5 | 71 |
| 152 | 51 | 4.8 | 11 |
| 153 | 58 | 8.6 | 7 |
| 156 | 125 | 6.0 | 21 |
| 164 | 954 | 3.7 | 258 |
| 165 | 462 | 3.5 | 132 |
| 166 | 603 | 4.5 | 134 |
| 167 | 357 | 4.2 | 85 |
| 168 | 823 | 6.6 | 125 |
| 176a | 79 | 0.6 | 132 |
| 188 | 118 | 0.5 | 236 |
| 193 | 121 | 1.3 | 93 |
| Rauwolscine | 392 | 4.2 | 93 |

The ability of compounds of the invention to inhibit biogenic amine uptake is determined as outlined below.

UPTAKE INHIBITION PROCEDURE a. Synaptosomal Preparation

Sprague-Dawley derived rats of either sex, weighing about 180-250 g, were killed by decapitation. The brains were immediately removed, placed on a glass plate chilled over crushed ice and dissected according to a modification of the method of Glowinski and Iversen (J. Neurochem. 13, 655-669, 1966). First, the rhombencephalon was separated by transverse section and discarded. The remaining tissue was bisected by a midline sagittal cut. The hypothalamus was removed using the anterior and posterior reference points, respectively. The hippocampus was peeled away and discarded and the striata were exposed and removed. Frontal cortical tissue was dissected from remaining brain structures. The hypothalamus and striatum each weighed about 100 mg, the striata 50-75 mg, and the cortex weighed up to 800 mg. The tissues were placed in a cold Potter-Elvehjem glass homogenizer with 5 (cortex) or 10 (hypothalamus) and 20 (striatum) volumes of ice-cold 0.32M sucrose, pH 7.0 and homogenized by hand. The homogenate was centrifuged at 2500 rpm in a GLC centrifuge for 10 minutes in a refrigerated room. The supernatant fraction containing the synaptosomes was decanted, mixed thoroughly, and kept on crushed ice for use in the uptake studies.

b. Uptake Studies

Uptake studies were conducted according to the method of Synder and Coyle (J. Pharmacol. Exp. Ther. 165, 78-86, 1969) with minor modifications. Usually a 0.1 ml aliquot of the synaptosomal preparation was incubated in a mixture of 0.75 ml of modified Krebs-Ringer buffer, 0.05 ml of the drug being evaluated for uptake inhibition, and 0.1 ml of a 1 μM tritiated amine (norepinephrine, serotonin or dopamine) solution (final concentration 0.1 μM) for a total volume of 1 ml. The modified Krebs-Ringer bicarbonate buffer used in these studies contained 118 mM NaCl, 4 mM KCl, 1.3 mM $CaCl_2$, 1.12 mM $KH_2PO_4$, 1.2 mM $MgSO_4$ and 24 mM NaHCO$_3$, with the addition of 5 mM glucose, 0.15 mM disodium EDTA, 12.5 μM pargyline and 1 mM ascorbic acid. Uptake was initiated by the addition of the tritiated amine, and the mixture was incubated at 37° C. in a Dubnoff Metabolic Shaking Incubator for 4 minutes. Control incubations without the test drug were conducted at 37° C. to determine total uptake and nonspecific binding at 0° C. to correct for the diffusion of the tritiated amine into the synaptosomes and/or binding. Filtration was used to terminate uptake and collect the synaptosomes. In the filtration technique the incubation mixture was diluted with 4 ml of ice-cold 0.9% NaCl and filtered through GF/B glass microfiber filters (Whatman) under gentle vacuum. The filters were subsequently washed four times with 5 ml of ice-cold 0.9% NaCl and transferred to glass scintillation vials. Soluene ® (500 ml) and IONIC FLUOR (Packard) scintillation fluid (3.5 ml) were added and the vials were placed in a mechanical shaker for 1 hour. All samples were cold and dark adapted and counted in a TriCarb ® (Packarad) Model 460 Liquid Scintillation Spectrometer. Corrections were automatically made for quenching by the external standard method and for luminescence. All results (see Table 2) are based on total radioactivity.

TABLE 2

Biogenic Amine Uptake Inhibition for Representative Compounds

| Example # | IC$_{50}$ (μM) | | |
|---|---|---|---|
| | Norephinephrine | Serotonin | Dopamine |
| 5 | 1.044 | 5.924 | 6.525 |
| 6b | 0.574 | 1.95 | 10.14 |
| 11 | 1.744 | 7.227 | 10.121 |
| 19 | 0.498 | 0.411 | 6.09 |
| 20c | 1.583 | 0.161 | 9.17 |
| 30 | 0.624 | 1.34 | 8.08 |
| 34 | 0.365 | 2.20 | 9.40 |
| 41 | 0.200 | 2.277 | 6.030 |
| 44 | 0.357 | 3.294 | 8.64 |
| 72 | 0.137 | 0.466 | 6.83 |
| 73 | 0.336 | 0.840 | 8.43 |
| 143a | 1.101 | 4.027 | 8.718 |
| 160 | 0.991 | 1.844 | 2.929 |
| 165 | 0.398 | 1.238 | 6.674 |
| 166 | 1.524 | 0.400 | 8.770 |
| 176a | 1.557 | 2.83 | 7.31 |
| Imipramine | 0.346 | 0.778 | 125.00 |

The results of this assay indicate that the compounds inhibit the uptake of biogenic amines. For comparative purposes, a standard biogenic amine uptake inhibitor (imipramine) is illustrated.

The compounds of the invention can be administered in any effective pharmaceutically acceptable form to warm blooded animals, e.g., in oral, parenteral or infusable dosaqe forms, or as a buccal or nasal spray. Suitable parenteral routes of administration include, for example, intramuscular, intravenous, intraperitoneal or subcutaneous administration of the compounds.

In addition to the active compounds, compositions according to this invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate.

Such compositions may also contain adjuvants such as preserving, wetting, emulsifying, and dispersing agents. They may be sterilized, for example, by filtration through a bacteria retaining filter, or by incorporating sterilizing aqents into the compositions. They can also be manufactured in the form of sterile solid compositions which can be dissolved in sterile water, or other sterile injectable medium, immediately before use.

Solid dosaqe forms for oral administration include capsules, tablets, pills, powders and granules. In such solid dosaqe forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions may also comprise adjuvants, such as wetting aqents, emulsifying and suspending agents, and sweetening, flavoring and perfuming agents.

Actual dosage levels of active ingredient in the compositions of the invention may be varied so as to obtain an amount of active ingredient effective to obtain a desired therapeutic response for a particular composition and method of administration. The selected dosage level therefore depends upon the desired therapeutic effect, on the route of administration, on the desired duration of treatment and other factors. Generally, dosage levels of about 0.1 to about 200, more preferably about 0.5 to about 150 and most preferably about 1 to about 125 mg of active ingredient per kg of body weight per day are administered orally to a mammalian patient suffering from depression. If desired, the daily dose may be divided into multiple doses for administration, e.g., two to four separate doses per day.

In addition to the above, the compounds of the invention can be administered as topical compositions. These compositions are preferably administered as topical pharmaceutical compositions suitable for ophthalmic administration, in a pharmaceutically acceptable vehicle such as pharmaceutically acceptable sterile aqueous or nonaqueous solutions, suspensions, emulsions, ointments or solid inserts.

Examples of suitable pharmaceutically acceptable vehicles for ophthalmic administration are water, propylene glycol and other pharmaceutically acceptable alcohols, sesame or peanut oil and other pharmaceutically acceptable vegetable oils, petroleum jelly, water soluble ophthalmologically acceptable non-toxic polymers such as methyl cellulose, carboymethyl cellulose salts, hydroxyethyl cellulose, hydroxypropyl cellulose; acrylates such as polyacrylic acid salts; ethylacrylates; polyacrylamides; natural products such as gelatin, alginates, pectins, tragacanth, karaya, agar, acacia; starch derivatives such as starch acetate, hydroxyethyl starch ethers, hydroxypropyl starch; as well as other synthetic derivatives such as polyvinyl alcohol, polyvinyl pyrrolidone, polyvinyl methy ether, polyethylene oxide, carbopol and xantham gum; and mixtures of these polymers. Such compositions may also contain adjuvants such as buffering, preserving, wetting, emulsifying and dispersing agents. Suitable preserving aqents include antibacterial agents such as quaternary ammonium compounds, phenylmercuric salts, benzyl alcohol, phenyl ethanol; and antioxidants such as sodium metabisulfite, butylated hyhdroxyanisole and butylated hydroxytoluene. Suitable buffering aqents include borate, acetate, gluconate and phosphate buffers.

The pharmaceutical ophthalmic compositors of the invention may also be in the form of a solid insert. A solid water soluble or water swellable polymer such as dextran, hydroxyloweralkyl dextran, carboymethyl dextran, hydroxyloweralkyl cellulose, loweralkyl cellulose, carboxymethyl cellulose, polyvinyl alcohol, dextrin, starch, polyvinyl pyrrolidone and polyalkylene glycols may be used as the carrier for the drug.

Dosage levels of the active compound in the compositions for treating glaucoma or reducing and/or controlling intraocular pressure may be varied so as to obtain a desired therapeutic response to a particular composition. Generally, the active compound will be administered as an isotonic aqueous solution of from about 0.00001 to about 1.0 (w/v) percent concentration. More preferably, the active compound will be administered as an isotonic aqueous solution of from about 0.00001 to about 0.3 (w/v) percent concentration.

The term "controlling intraocular pressure" as used herein means the regulation, attenuation and modulation of increased intraocular tension. The term also means that the decrease in the otherwise elevated intraocular pressure obtained by the methods and compositions of the invention is maintained for a significant period of time as, for example, between consecutive doses of the composition of the invention.

The effect on intraocular pressure of the compounds of the invention can be determined in rabbits by using the following method.

EFFECTS OF TOPICALLY ADMINISTERED COMPOUNDS ON INTRAOCULAR PRESSURE OF RABBITS a. Method The intraocular pressure lowering effects of the compounds were evaluated in unanesthetized male albino, New Zealand rabbits weighing 2.0 to 2.5 kg. The rabbits were placed in Plas Labs restraining devices for the duration of the experiment. Intraocular pressure (IOP) was measured with a Bausch and Lomb Applamatic Tonometer and recorded as the average of three individual readings at each time point in the experiment. Baseline IOP values were established at three time points separated by 30 minutes. Each compound or vehicle was applied topically to the cornea in a volume of 0.1 ml to one eye in each six rabbits. The contralateral eye was untreated. IOP was recorded at 5, 15, 30, 60 and 90 minutes after dosing. The results obtained show that the compounds are able to reduce intraocular pressure in vivo.

b. Results

| % Change in Intraocular Pressure After Treatment (0.3% soln.) Compared to Untreated Eye in Rabbits | | | | | |
|---|---|---|---|---|---|
| Compound of | (Minutes) | | | | |
| Example | 5 | 15 | 30 | 60 | 90 |
| Vehicle | +1 | +7 | −3 | +13 | +9 |
| 10 | −45 | −31 | −25 | −36 | −23 |
| 11 (HCl salt) | −38 | −55 | −54 | −44 | −20 |

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compuond of the formula:

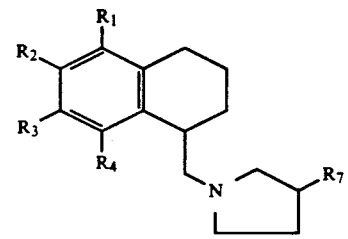

wherein
R$_1$, is selected from the group consisting of
hydrogen,
halo,
lower alkyl,
lower alkoxy,
thioalkoxy,
R$_2$, is lower alkoxy;
R$_3$, and R$_4$ are independently selected from
amino,
alkylamino of from one to three carbon atoms,
alkylsulfonylamino of from one to three carbon atoms,
R$_7$ is phenyl, thienyl, furyl, or substituted phenyl wherein the phenyl ring is substituted with methylenedioxy, ethylenedioxy, or with one, two or three substituents independently selected from loweralkyl, halo, hydroxy, loweralkoxy, amino, and thioalkyl; or a pharmaceutically acceptable salt thereof.

2. A pharmaceutical composition comprising a therapeutically effective amount of a compound as defined by claim 1 in combination with a pharmaceutically acceptable carrier.

3. A method of treating depression comprising administering to a host mammal in need of such treatment a therapeutically effective amount of a compound as defined by claim 1.

4. A method of treating glaucoma or controlling intraocular pressure comprising administering to a host mammal in need of such treatment a therapeutically effective amount of a compound as defined by claim 1.

5. A method of selectively inhibiting alpha-2-adrenergic receptors comprising administering to a host mammal in need of such treatment a therapeutically effective amount of a compound as defined by claim 1.

* * * * *